US011596416B2

(12) United States Patent
Stokes et al.

(10) Patent No.: US 11,596,416 B2
(45) Date of Patent: Mar. 7, 2023

(54) SURGICAL CLIP APPLIER WITH PARALLEL CLOSURE JAWS

(71) Applicant: CILAG GMBH INTERNATIONAL, Zug (CH)

(72) Inventors: Michael J. Stokes, Cincinnati, OH (US); Gregory Scott, Cincinnati, OH (US); Disha Labhasetwar, Cincinnati, OH (US); John Brady, Cincinnati, OH (US)

(73) Assignee: CILAG GMBH INERNATIONAL, Zug (CH)

( * ) Notice: Subject to any disclaimer, the term of this patent is extended or adjusted under 35 U.S.C. 154(b) by 125 days.

(21) Appl. No.: 17/002,007

(22) Filed: Aug. 25, 2020

(65) Prior Publication Data

US 2020/0383686 A1    Dec. 10, 2020

Related U.S. Application Data

(62) Division of application No. 15/891,594, filed on Feb. 8, 2018, now Pat. No. 10,779,839.

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 34/25* (2016.02);
(Continued)

(58) Field of Classification Search
CPC .............. A61B 17/122; A61B 17/1285; A61B 2017/00473; A61B 2017/00477;
(Continued)

(56) References Cited

U.S. PATENT DOCUMENTS

| 5,336,232 A | 8/1994 | Green et al. |
| 6,582,451 B1 | 6/2003 | Marucci et al. |

(Continued)

FOREIGN PATENT DOCUMENTS

| EP | 0 559 481 | 9/1993 |
| EP | 3 117 781 A1 | 1/2017 |

(Continued)

*Primary Examiner* — Ryan J. Severson
(74) *Attorney, Agent, or Firm* — Vorys, Sater, Seymour and Pease LLP

(57) ABSTRACT

An end effector for a surgical clip applier includes a housing, and jaws that include opposed first and second jaw members each comprising an independent structure movable relative to the other, the first jaw member defining a first inner surface and the second jaw member defining a second inner surface opposite the first inner surface. An actuation mechanism is arranged within the housing and is operable to move the jaws between an open position and a closed position, the actuation mechanism including a linear drive that provides transition pins engageable with angled slots defined in the first and second jaw members. Linear movement of the linear drive moves the jaws between the open and closed positions, and the first and second inner surfaces remain substantially parallel to each other as the jaws move between the open and closed positions.

17 Claims, 11 Drawing Sheets

(51) Int. Cl.
*A61B 34/00* (2016.01)
*A61B 34/37* (2016.01)
*A61B 17/29* (2006.01)
*A61B 17/10* (2006.01)
*A61B 34/30* (2016.01)
*A61B 17/00* (2006.01)

(52) U.S. Cl.
CPC .............. *A61B 34/37* (2016.02); *A61B 34/71* (2016.02); *A61B 17/10* (2013.01); *A61B 34/70* (2016.02); *A61B 2017/00473* (2013.01); *A61B 2017/00477* (2013.01); *A61B 2017/2936* (2013.01); *A61B 2017/2937* (2013.01); *A61B 2017/2939* (2013.01); *A61B 2017/2944* (2013.01); *A61B 2034/305* (2016.02)

(58) Field of Classification Search
CPC ......... A61B 34/25; A61B 34/37; A61B 34/70; A61B 34/71; A61B 2034/305
See application file for complete search history.

(56) References Cited

U.S. PATENT DOCUMENTS

| | | | | |
|---|---|---|---|---|
| 8,216,257 | B2 * | 7/2012 | Huitema | A61B 17/0682 |
| | | | | 606/142 |
| 8,403,945 | B2 | 3/2013 | Whitfield et al. | |
| 8,568,443 | B1 * | 10/2013 | Jackman | A61B 17/00 |
| | | | | 606/205 |
| 9,232,979 | B2 | 1/2016 | Parihar et al. | |
| 9,364,239 | B2 * | 6/2016 | Malkowski | A61B 17/1285 |
| 9,855,043 | B2 * | 1/2018 | Malkowski | A61B 17/1285 |
| 9,861,371 | B2 * | 1/2018 | Martin | A61B 17/1227 |
| 10,039,548 | B2 * | 8/2018 | Parihar | A61B 34/37 |
| 10,245,059 | B2 * | 4/2019 | Hernandez Juanpera | |
| | | | | A61B 34/70 |
| 10,258,359 | B2 * | 4/2019 | Kapadia | A61B 17/29 |
| 10,285,763 | B2 * | 5/2019 | Vale | A61B 34/30 |
| 10,292,712 | B2 * | 5/2019 | Shankarsetty | A61B 17/1285 |
| 10,390,853 | B2 * | 8/2019 | Kapadia | A61B 34/74 |
| 10,631,874 | B2 * | 4/2020 | Martin | A61B 17/122 |
| 10,667,873 | B2 * | 6/2020 | Wallace | A61B 34/71 |
| 10,779,839 | B2 * | 9/2020 | Stokes | A61B 17/1285 |
| 10,779,846 | B2 * | 9/2020 | Williams | A61B 17/29 |
| 11,116,534 | B2 * | 9/2021 | Kapadia | A61B 34/71 |
| 11,253,170 | B2 * | 2/2022 | Ziemek | A61B 17/02 |
| 2011/0224696 | A1 | 9/2011 | Huitema et al. | |
| 2013/0310849 | A1 * | 11/2013 | Malkowski | A61B 17/128 |
| | | | | 606/142 |
| 2016/0213377 | A1 * | 7/2016 | Shankarsetty | A61B 17/1285 |
| 2016/0249926 | A1 * | 9/2016 | Malkowski | A61B 17/128 |
| | | | | 606/142 |
| 2016/0287252 | A1 | 10/2016 | Parihar | |
| 2016/0310156 | A1 * | 10/2016 | Kapadia | B25J 15/0233 |
| 2017/0014136 | A1 * | 1/2017 | Martin | A61B 17/1285 |
| 2017/0014137 | A1 * | 1/2017 | Martin | A61B 17/1285 |
| 2017/0020616 | A1 * | 1/2017 | Vale | A61B 34/30 |
| 2017/0027598 | A1 * | 2/2017 | Hernandez Juanpera | |
| | | | | A61B 17/29 |
| 2017/0224367 | A1 * | 8/2017 | Kapadia | A61B 17/29 |
| 2017/0231653 | A1 * | 8/2017 | Kapadia | A61B 34/71 |
| | | | | 606/208 |
| 2018/0153629 | A1 * | 6/2018 | Wallace | A61B 34/71 |
| 2019/0133630 | A1 * | 5/2019 | Williams | A61B 17/29 |
| 2019/0239890 | A1 * | 8/2019 | Stokes | A61B 34/37 |
| 2020/0383686 | A1 * | 12/2020 | Stokes | A61B 17/122 |

FOREIGN PATENT DOCUMENTS

| | | |
|---|---|---|
| EP | 3 132 759 A1 | 2/2017 |
| WO | 2016209788 A1 | 12/2016 |

* cited by examiner

SURGICAL CLIP APPLIER WITH PARALLEL CLOSURE JAWS

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which a small incision is formed in the abdomen of a patient and a trocar is inserted through the incision to form a surgical access pathway for a surgical tool and elongate shaft. Once located within the abdomen, the surgical tool engages and/or treats tissue in a number of ways to achieve a diagnostic or therapeutic effect. Manipulation and engagement of the surgical tool may take place via various components passing through the elongate shaft.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip or "ligation clip" therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical systems and, more particularly, to surgical clip appliers with improved jaws that facilitate parallel closure of opposed jaw members.

Embodiments discussed herein describe improvements to end effector jaws used in surgical clip appliers. As described herein, an end effector may include a housing and jaws may extend out a distal end of the housing. The jaws include opposed first and second jaw members, each comprising an independent structure that is movable relative to the other. The first and second jaw members each define opposing inner surfaces and an actuation mechanism may be operatively coupled to the jaw members to transition the jaws between an open position and a closed position. Since the jaw members comprise independent and separate structures, the opposing inner surfaces are able to remain parallel to each other as the jaws move between the open and closed positions and thereby achieve parallel closure.

Figure 1:
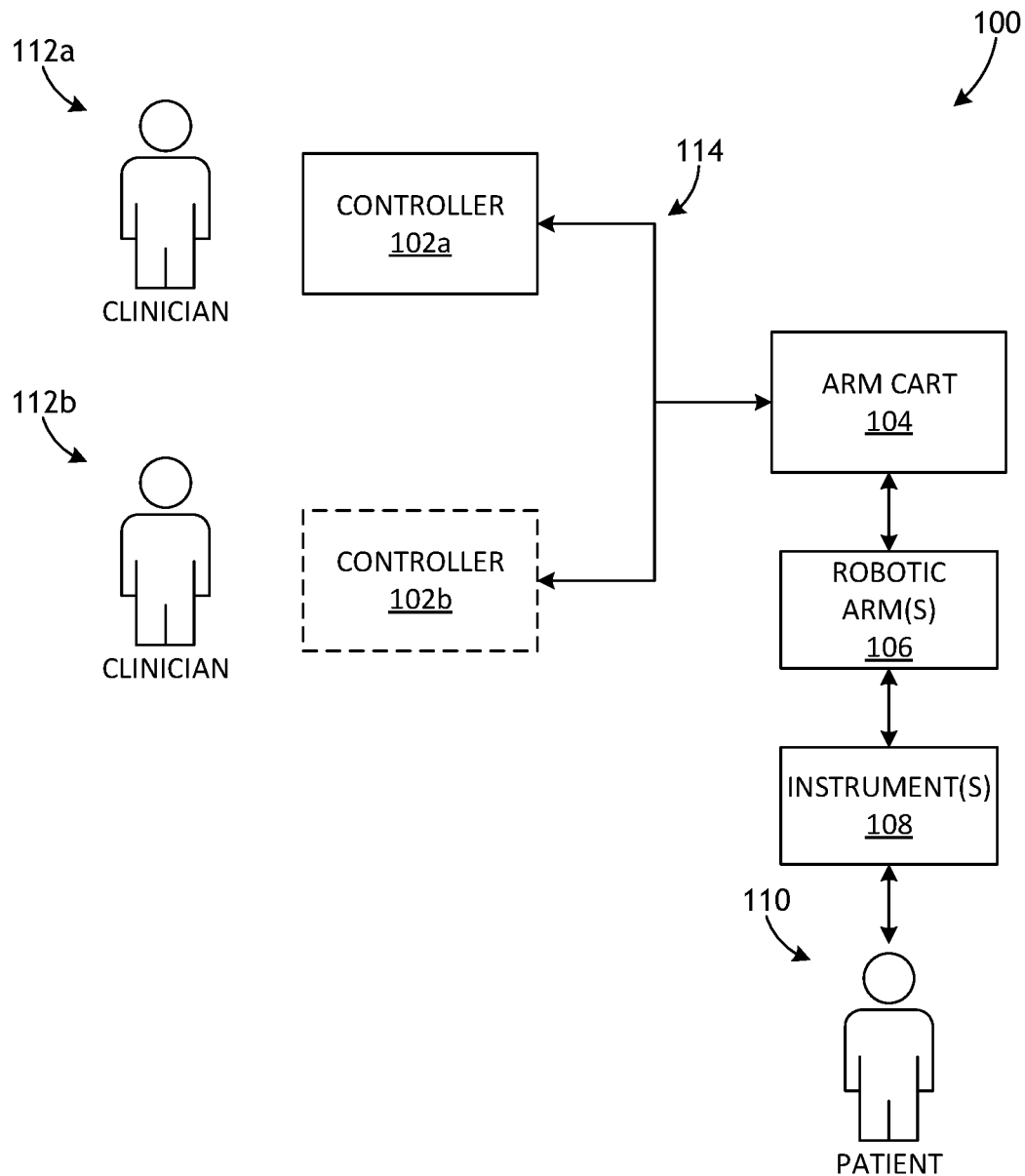
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102*a* and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112*a* (e.g., a surgeon) from the master controller 102*a*.

In some embodiments, a second master controller 102*b* (shown in dashed lines) operated by a second clinician 112*b* may also direct operation of the robotic arms 106 and instruments 108 in conjunction with the first clinician 112*a*. In such embodiments, for example, each clinician 102*a,b* may control different robotic arms 106 or, in some cases, complete control of the robotic arms 106 may be passed between the clinicians 102*a,b*. In some embodiments, additional arm carts (not shown) having additional robotic arms (not shown) may be utilized during surgery on a patient 110, and these additional robotic arms may be controlled by one or more of the master controllers 102*a,b*.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
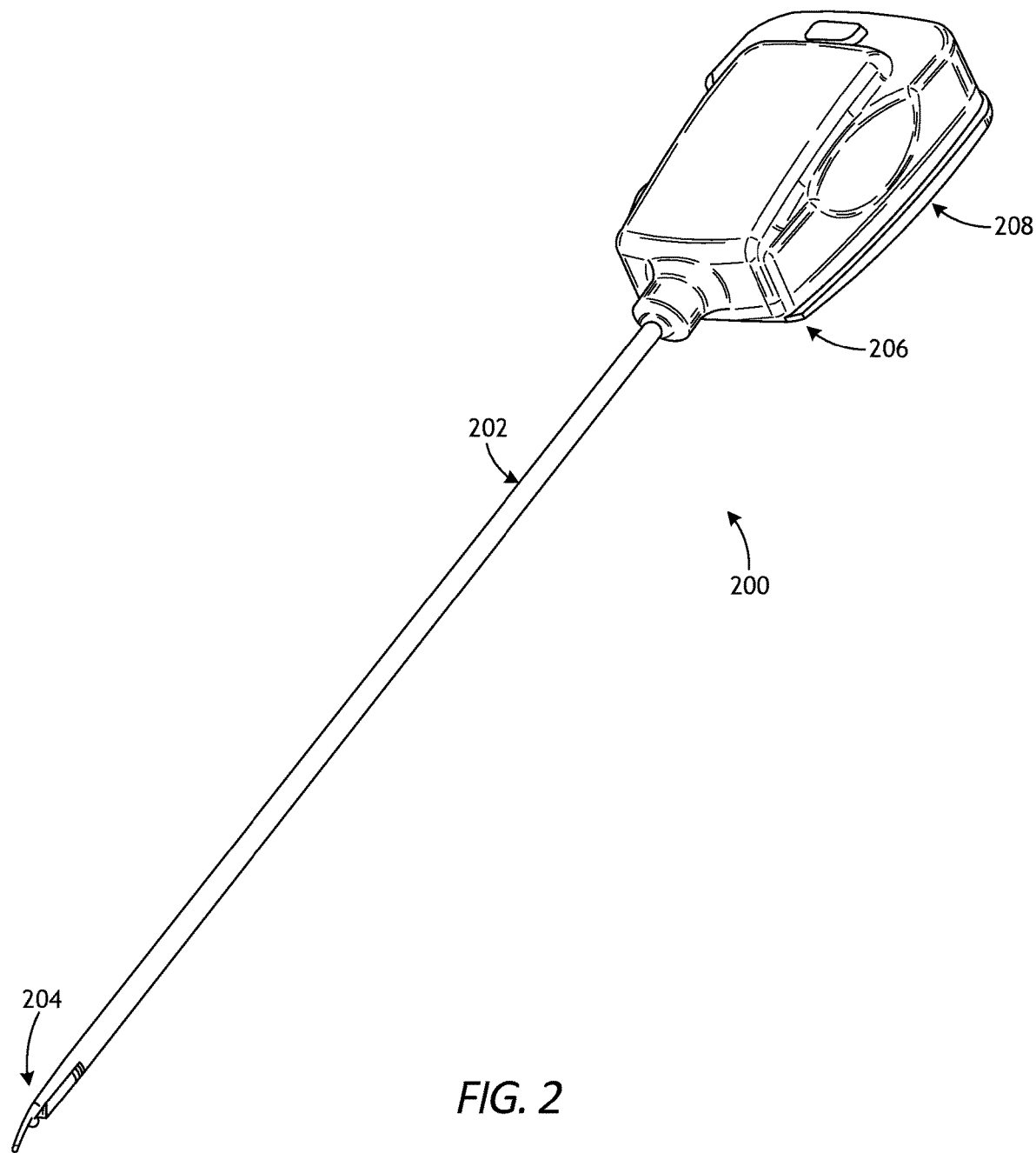
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in U.S. Patent Pub. 2016/0287252, entitled "Clip Applier Adapted for Use with a Surgical Robot," the contents of which are hereby incorporated by reference in their entirety.

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
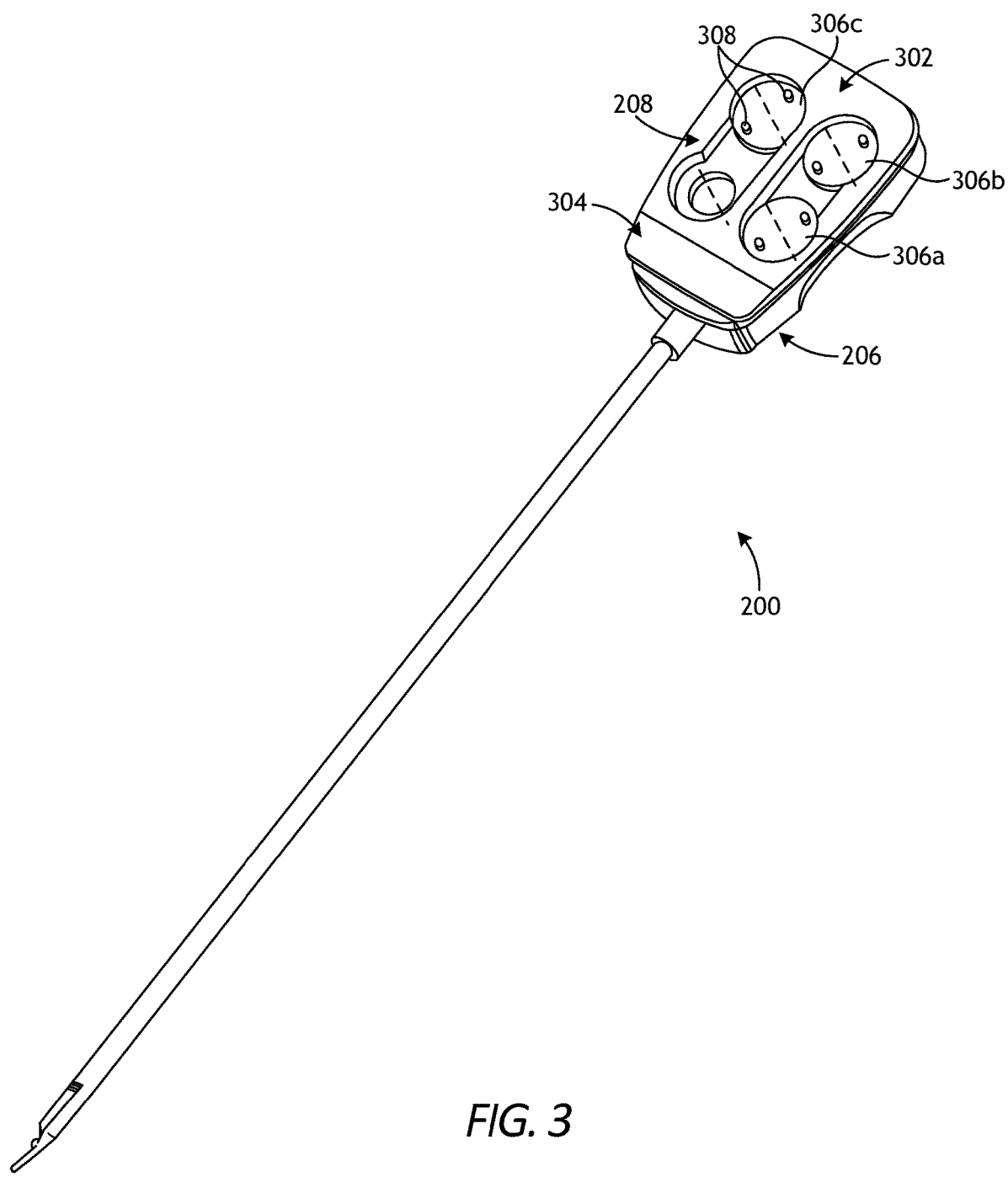
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
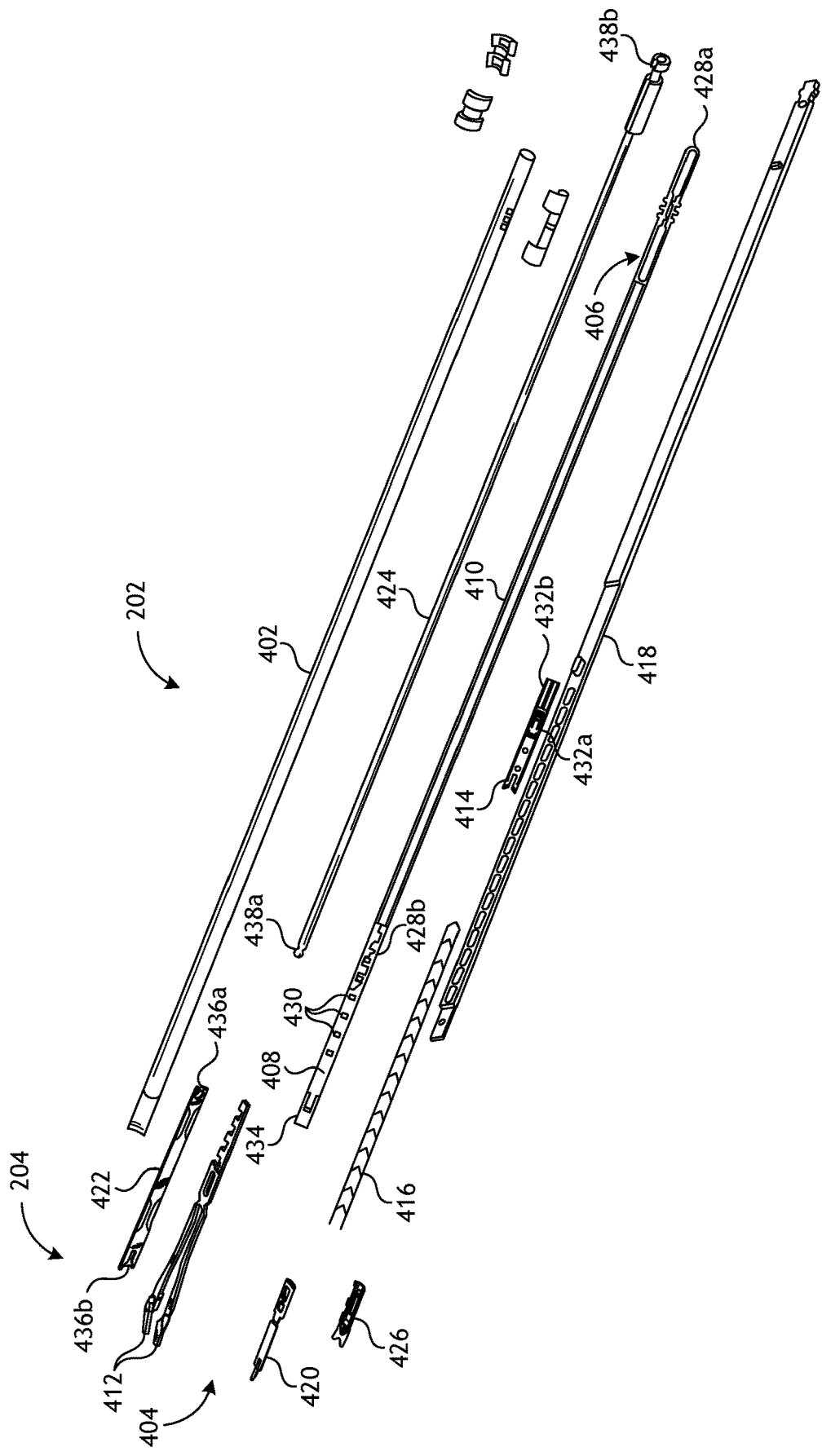
FIG. 4 is an exploded view of the elongate shaft and the end effector of the surgical tool of FIGS. 2 and 3.

FIG. 4 is an exploded view of one example of the elongate shaft 202 and the end effector 204 of the surgical tool 200 of FIGS. 2 and 3, according to one or more embodiments. As illustrated, the shaft 202 includes an outer tube 402 that houses the various components of the shaft 202, which can include a jaw retaining assembly 404. The jaw retaining assembly 404 includes a jaw retainer shaft 406 with a clip track 408 and a push rod channel 410 formed thereon. The end effector 204 includes opposing jaws 412 that are configured to mate to a distal end of the clip track 408.

The shaft 202 also includes a clip advancing assembly, which, in one example embodiment, can include a feeder shoe 414 adapted to be slidably disposed within the clip track 408. The feeder shoe 414 is designed to advance a series of clips 416 positioned within the clip track 408, and a feedbar 418 is adapted to drive the feeder shoe 414 through the clip track 408. An advancer assembly 420 is adapted to mate to a distal end of the feedbar 418 for advancing a distal-most clip into the jaws 412.

The shaft 202 furthers include a clip forming or camming assembly operable to collapse the jaws 412 and thereby crimp (crush) a surgical clip 416 positioned between (interposing) the jaws 412. The camming assembly includes a cam 422 that slidably mates to the jaws 412, and a push rod 424 that moves the cam 422 relative to the jaws 412 to collapse the jaws 412. A tissue stop 426 can mate to a distal end of the clip track 408 to help position the jaws 412 relative to a surgical site.

The jaw retainer shaft 406 is extendable within and couples to the outer tube 402 at a proximal end 428a, and its distal end 428b is adapted to mate with the jaws 412. The push rod channel 410 formed on the jaw retainer shaft 406 may be configured to slidably receive the push rod 424, which is used to advance the cam 422 over the jaws 412. The clip track 408 extends distally beyond the distal end 428b of the jaw retainer shaft 406 to allow a distal end of the clip track 408 to be substantially aligned with the jaws 412.

The clip track 408 can include several openings 430 formed therein for receiving an upper or "superior" tang 432a formed on the feeder shoe 414 adapted to be disposed within the clip track 408. The clip track 408 can also include a stop tang 434 formed thereon that is effective to be engaged by a corresponding stop tang formed on the feeder shoe 414 to prevent movement of the feeder shoe 414 beyond a distal-most position. To facilitate proximal movement of the feeder shoe 414 within the clip track 408, the feeder shoe 414 can also include a lower or "inferior" tang 432b formed on the underside thereof for allowing the feeder shoe 414 to be engaged by the feedbar 418 as the feedbar 418 is moved distally. In use, each time the feedbar 418 is moved distally, a detent formed in the feedbar 418 engages the inferior tang 432b and moves the feeder shoe 414 distally a predetermined distance within the clip track 408. The feedbar 418 can then be moved proximally to return to its initial position, and the angle of the inferior tang 432b allows the inferior tang 432b to slide into the next detent formed in the feedbar 418.

The jaws 412 include first and second opposed jaw members that are movable (collapsible) relative to one another and are configured to receive a surgical clip from the series of clips 416 therebetween. The jaw members can each include a groove formed on opposed inner surfaces thereof for receiving the legs of a surgical clip 416 in alignment with the jaw members. In the illustrated embodiment, the jaw members are biased to an open position and a force is required to urge the jaw members toward one another to crimp the interposing clip 416. The jaw members can also each include a cam track formed thereon for allowing the cam 422 to slidably engage and move the jaw members toward one another. A proximal end 436a of the cam 422 is matable with a distal end 438a of the push rod 424, and a distal end 436b of the cam 422 is adapted to engage and actuate the jaws 412. The proximal end 438b of the push rod 424 is matable with a closure link assembly associated with the drive housing 206 for moving the push rod 424 and the cam 422 relative to the jaws 412.

The distal end 436b of the cam 422 includes a camming channel or tapering recess formed therein for slidably receiving corresponding cam tracks provided by the jaw members. In operation, the cam 422 is advanced from a proximal position, in which the jaw members are spaced apart from one another, to a distal position, where the jaw members are collapsed to a closed position. As the cam 422 is advanced over the jaw members, the tapering recess at the distal end 436b serves to push the jaw members toward one another, thereby crimping a surgical clip 416 disposed therebetween.

Figure 5:
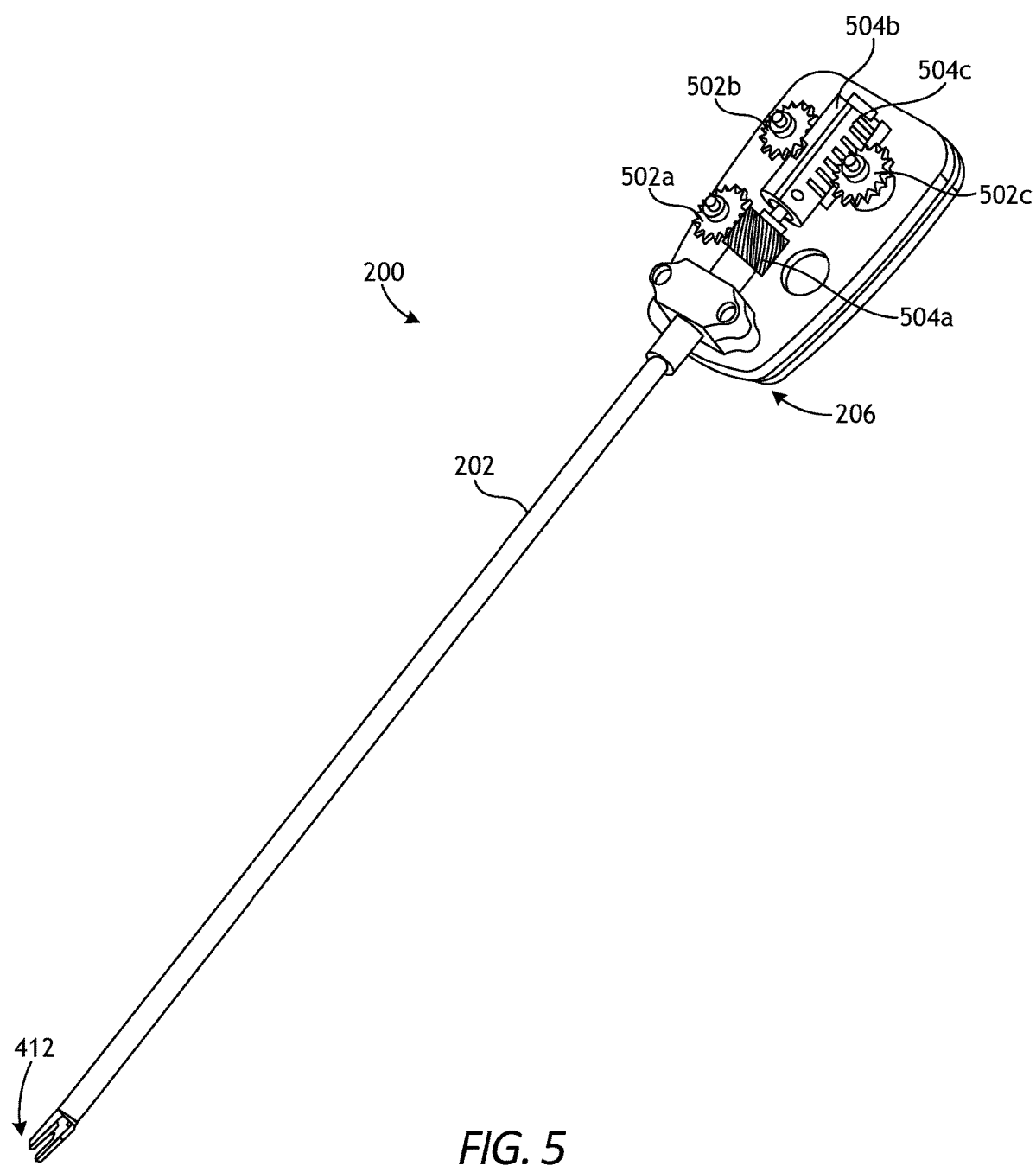
FIG. 5 is an exposed isometric view of the surgical tool of FIG. 2.

FIG. 5 is an exposed isometric view of the surgical tool 200 of FIG. 2, according to one or more embodiments. The shroud or covering of the drive housing 206 has been removed to reveal the internal component parts. As illustrated, the surgical tool 200 may include a first drive gear 502a, a second drive gear 502b, and a third drive gear 502c. The first drive gear 502a may be operatively coupled to (or extend from) the first drive input 306a (FIG. 3) such that actuation of the first drive input 306a correspondingly rotates the first drive gear 502a. Similarly, the second and third drive gears 502b,c may be operatively coupled to (or extend from) the second and third drive inputs 306b,c (FIG. 3), respectively, such that actuation of the second and third drive inputs 306b,c correspondingly rotates the second and third drive gears 502b,c, respectively.

The first drive gear 502a may be configured to intermesh with a first driven gear 504a, which is operatively coupled to the shaft 202. In the illustrated embodiment, the driven gear 504a comprises a helical gear. In operation, rotation of the first drive gear 502a about a first axis correspondingly rotates the first driven gear 504a about a second axis orthogonal to the first axis to control rotation of the shaft 202 in clockwise and counter-clockwise directions based on the rotational direction of the first drive gear 502a.

The second drive gear 502b may be configured to intermesh with a second driven gear 504b (partially visible in FIG. 5), and the third drive gear 502c may be configured to intermesh with a third driven gear 504c. In the illustrated embodiment, the second and third drive and driven gears 502b,c, 504b,c comprise corresponding rack and pinion interfaces, where the driven gears 504b,c comprise the rack and the drive gears 502b,c comprise the pinion. Independent rotation of the second and third drive gears 502b,c will cause the second and third driven gears 504b,c, respectively, to translate linearly relative to (independent of) one another.

In at least one embodiment, actuation (rotation) of the third drive gear 502c will result in a surgical clip 416 (FIG. 4) being fed into the jaws 412. More particularly, the third driven gear 504c may be operatively coupled to the feedbar 418 (FIG. 4) and, upon rotation of the third drive gear 502c in a first angular direction, the third driven gear 504c will advance distally and correspondingly advance the feedbar 418 a sufficient distance to fully advance a surgical clip into the jaws 412. Rotation of the third drive gear 502c may be precisely controlled by an electrical and software interface to deliver the exact linear travel to the third driven gear 504c necessary to feed a clip 416 into the jaws 412.

Upon delivery of a clip into the jaws 412, or after a predetermined amount of rotation of the third drive gear 502c, rotation of the third drive gear 502c is reversed in a second angular direction to move the third driven gear 504c linearly in a proximal direction, which correspondingly moves the feedbar 418 proximally. This process may be repeated several times to accommodate a predetermined number of clips residing in the shaft 202.

Actuation of the second drive gear 502b causes the jaws 412 to close or collapse to crimp a surgical clip. More particularly, the second driven gear 504b may be coupled to the proximal end 438b (FIG. 4) of the push rod 424 (FIG. 4) and, upon actuation of the second drive gear 502b in a first angular direction, the second driven gear 504b will be advanced linearly in a distal direction and correspondingly drive the push rod 424 distally, which drives the cam 422 over the jaws 412 to collapse the jaw members and crimp a surgical clip positioned in the jaws 412. Once a surgical clip is successfully deployed, rotation of the second drive gear 502b is reversed in the opposite angular direction to move the second driven gear 504b in a proximal direction, which correspondingly moves the push rod 424 and the cam 422 proximally and permits the jaws 412 to open once again.

The processes of delivering a surgical clip into the jaws 412 and collapsing the jaws 412 to crimp the surgical clip are not limited to the actuation mechanisms and structures described herein. In alternative embodiments, for example, the second and third driven gears 504b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing the feedbar 418 to deliver a surgical clip into the jaws 412 and advancing the cam 422 to collapse the jaws 412 and crimp the surgical clip.

Figure 6:
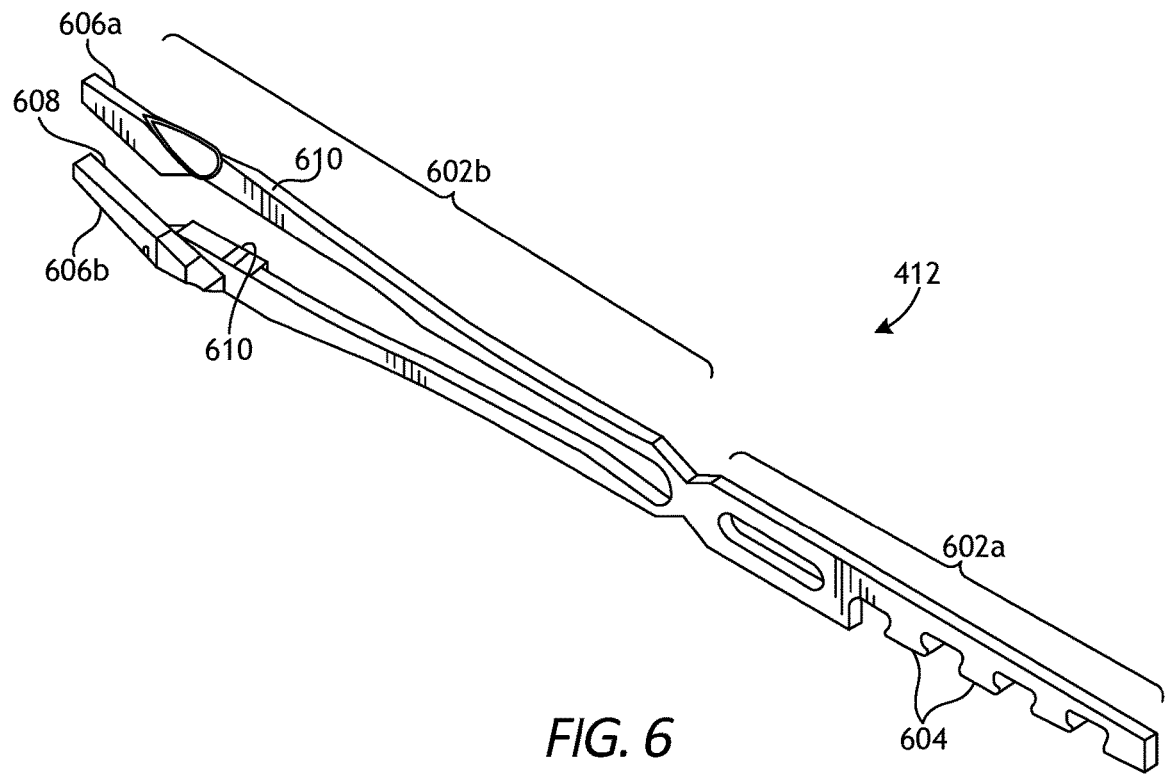
FIG. 6 is an enlarged, isometric view of one example of the jaws of FIG. 8.

FIG. 6 is an enlarged, isometric view of one example of the jaws 412 of FIG. 4. As illustrated, the jaws 412 include a proximal portion 602a and a distal portion 602b. The proximal portion 602a provides teeth 604 for mating with corresponding teeth formed on the jaw retainer shaft 406 (FIG. 4). Other techniques, however, can be used to mate the jaws 412 to the jaw retainer shaft 406; e.g., a dovetail connection, a male-female connection, etc. Alternatively, the jaws 412 may be integrally formed with the jaw retainer shaft 406.

The distal portion 602b of the jaws 412 provides opposed first and second jaw members 606a and 606b movable relative to one another and adapted to receive a surgical clip (not shown) therebetween. In at least one embodiment, the jaw members 606a,b are biased to an open position, and a force is required to move the jaw members 606a,b toward one another (i.e., collapse the jaws 412). Each jaw member 606a,b can include a groove 608 (one partially shown in FIG. 6) formed on opposed inner surfaces thereof for receiving the legs of a surgical clip in alignment with the jaw members 606a,b. Each jaw member 606a,b can also include a cam track 610 formed thereon. The cam 422 (FIG. 4) may be configured to engage the jaw members 606a,b at the cam tracks 610 and thereby urge (force) the jaw members 606a,b to collapse toward one another. In the illustrated embodiment, the cam tracks 610 are essentially ramped features formed on a superior (upper) surface of each jaw member 606a,b. In other embodiments, however, the cam tracks 610 may be formed and otherwise provided on the outer lateral sides of each jaw member 606a,b, without departing from the scope of the disclosure.

Figure 7:
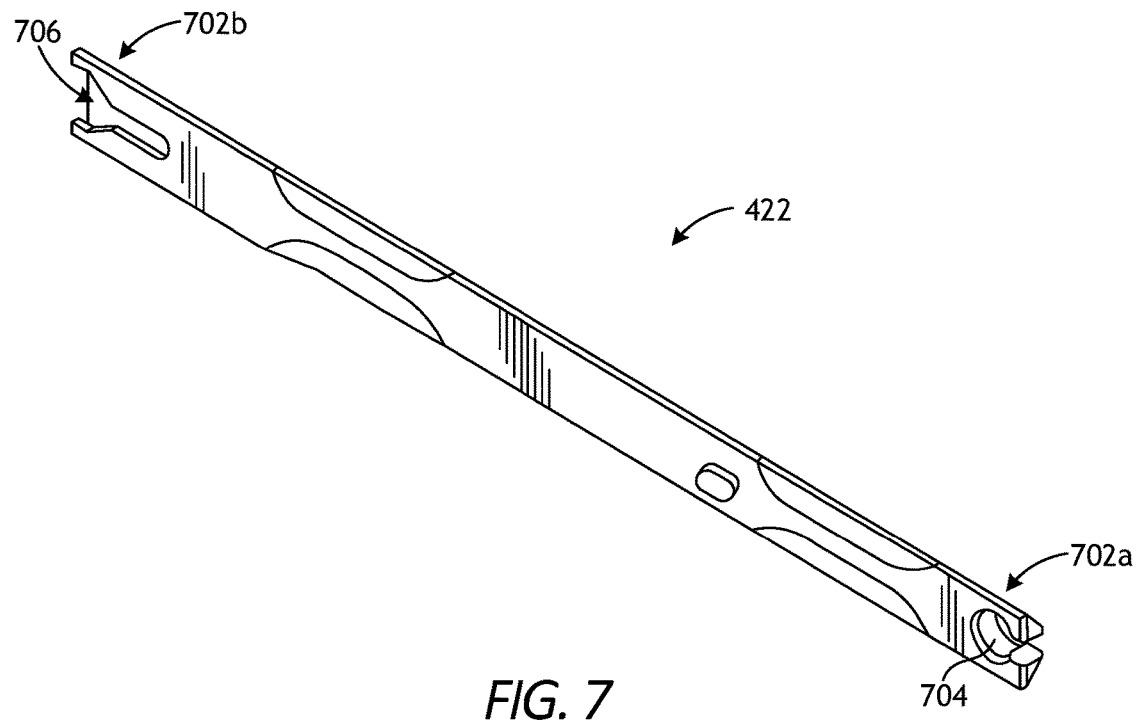
FIG. 7 is an enlarged isometric view of one example of the cam of FIG. 8.
Figure 8:
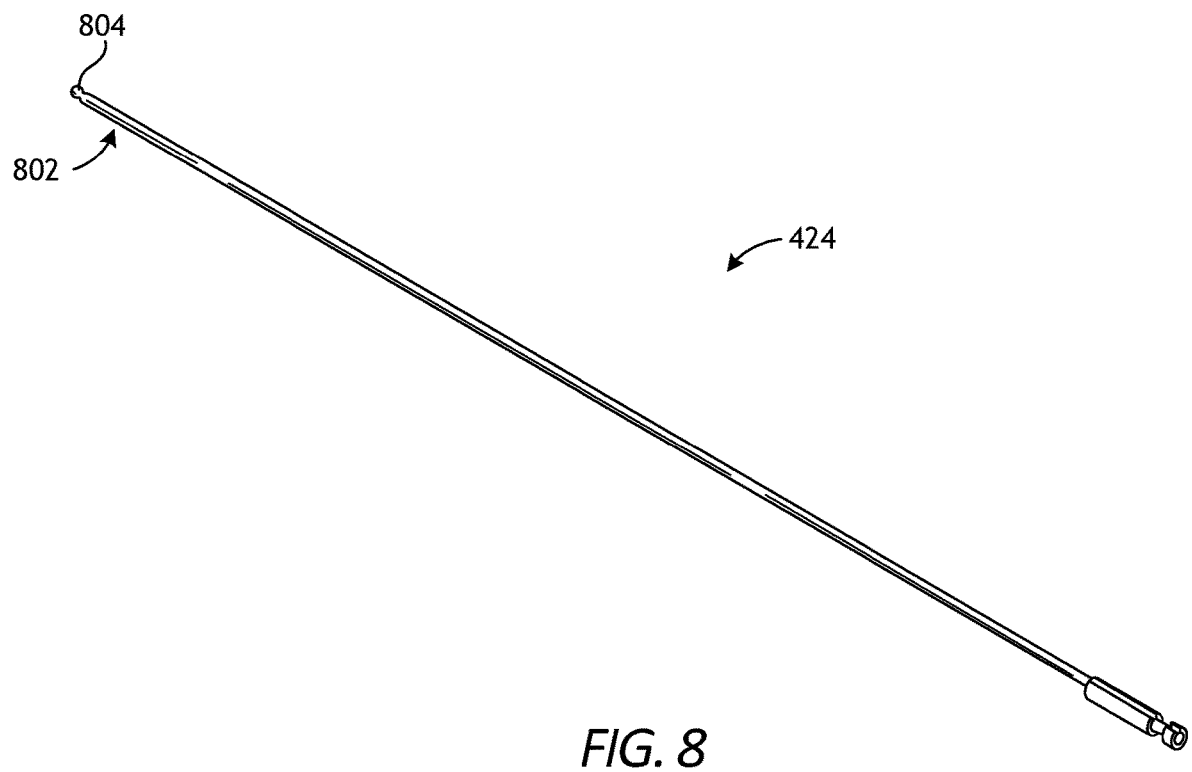
FIG. 8 is an isometric view of one example of the push rod of FIG. 8.

FIG. 7 is an enlarged isometric view of one example of the cam 422 of FIG. 4, and FIG. 8 is an isometric view of one example of the push rod 424 of FIG. 4. The cam 422 may be configured for slidably mating with and engaging the jaw members 606a,b (FIG. 6). In at least one embodiment, a proximal end 702a of the cam 422 is matable with a distal end 802 (FIG. 8) of the push rod 424. As illustrated, the proximal end 702a of the cam 422 provides a female or keyed cut-out 704 (FIG. 7) formed therein to receive a male or key member 804 (FIG. 8) formed at the distal end 802 of the push rod 424. As will be appreciated, the cam 422 and the push rod 424 may alternatively be integrally formed with one another. The proximal end 802 of the push rod 424 can be adapted to mate to a closure link assembly for moving the push rod 424 and the cam 422 relative to the jaws 412 (FIG. 6).

Referring to FIG. 7, the distal end 702b of the cam 422 is adapted to engage and actuate the jaws 412 (FIG. 6). More specifically, in the illustrated embodiment, a camming channel or tapering recess 706 is formed or otherwise provided at the distal end 702b of the cam 422. During actuation, the tapering recess 706 is configured to slidably receive the cam tracks 610 (FIG. 6) provided by the jaw members 606a,b (FIG. 6), and further movement of the cam 422 relative to the jaws 412 will urge the jaw members 606a,b to collapse toward each other.

Figure 9A:
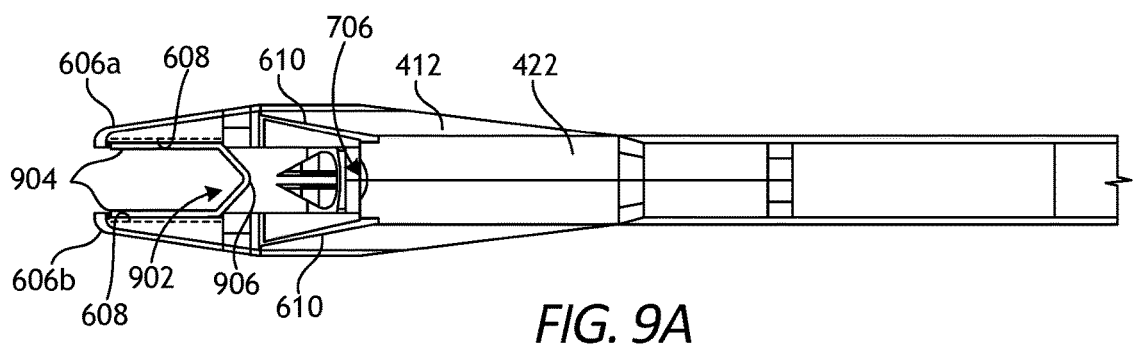
FIGS. 9A and 9B illustrate example operation of the cam and the jaws.
Figure 9B:
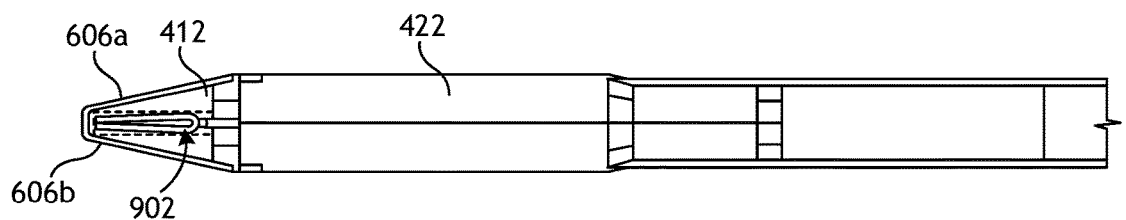

FIGS. 9A and 9B illustrate example operation of the cam 422 and the jaws 412. In FIG. 9A, a surgical clip 902 has been previously advanced to the jaws 412. As illustrated, the legs 904 of the surgical clip 902 are received within the grooves 608 defined in the opposed inner surfaces of the jaw members 606a,b, and the crown 906 (alternately referred to as the "apex") is positioned between the jaw members 606a,b and points proximally.

To crimp the surgical clip 902, the cam 422 is advanced distally (i.e., to the left in FIGS. 9A and 9B) relative to the jaws 412. In FIG. 9A, the cam 422 is shown in a proximal position, where the jaw members 606a,b are spaced apart from one another. As the cam 422 is advanced distally over the jaw members 606a,b, the tapering recess 706 receives and slidingly engages the angled surfaces of the cam tracks 610, which simultaneously urges the jaw members 606a,b to collapse toward one another and crimp the surgical clip 902. FIG. 9B shows the crimped surgical clip 902.

During distal movement of the cam 422, the jaw members 606a,b act as individual cantilever beams as they are urged toward one another by the cam 422. Because the jaw members 606a,b act as cantilever beams, the distal ends or "tips" of the jaw members 606a,b come together first, at which point each jaw member 606a,b is effectively converted into a fixed-pinned beam, which increases the stiffness of the system. As opposed pinned-pinned beams, the lateral force required to fully close the jaw members 606a,b along the length of the grooves 608 increases dramatically. In some applications, for example, 70 lbf-80 lbf of force is required to fully close the jaw members 606a,b. Consequently, this requires more expensive and powerful actuators to move (actuate) the cam 422 and necessitates more robust materials used to make the jaws 412, the cam 422, and other intervening structural elements that facilitate jaw 812 actuation.

According to embodiments of the present disclosure, robotic clip appliers (or alternately non-robotic clip appliers) may incorporate improved jaws that eliminate distal tip-to-tip closure of its corresponding jaw members. As described herein, the improved jaws may be designed to achieve parallel (or substantially parallel) closure between the corresponding jaw members. As used herein, the term "substantially parallel" can refer to true relative parallelism between opposing members or near true relative parallelism, without departing from the scope of the disclosure. Eliminating tip-to-tip closure eliminates the need to deflect the opposed jaw members between supported ends, which may prove advantageous in eliminating the additional reaction load from the opposing jaw member and minimizing jaw length. Moreover, substantial parallel closure between opposed jaw members may prove advantageous in reducing manufacturing costs. Conventional clip applier jaws, for example, are typically manufactured of robust materials via stamping or machining processes to accommodate the large forces required to fully close the jaws. Jaws capable of facilitating parallel closure of opposed jaw members, however, may require less force to fully close, which allows the jaws to be manufactured of less expensive materials and via less expensive manufacturing processes.

Figure 10A:
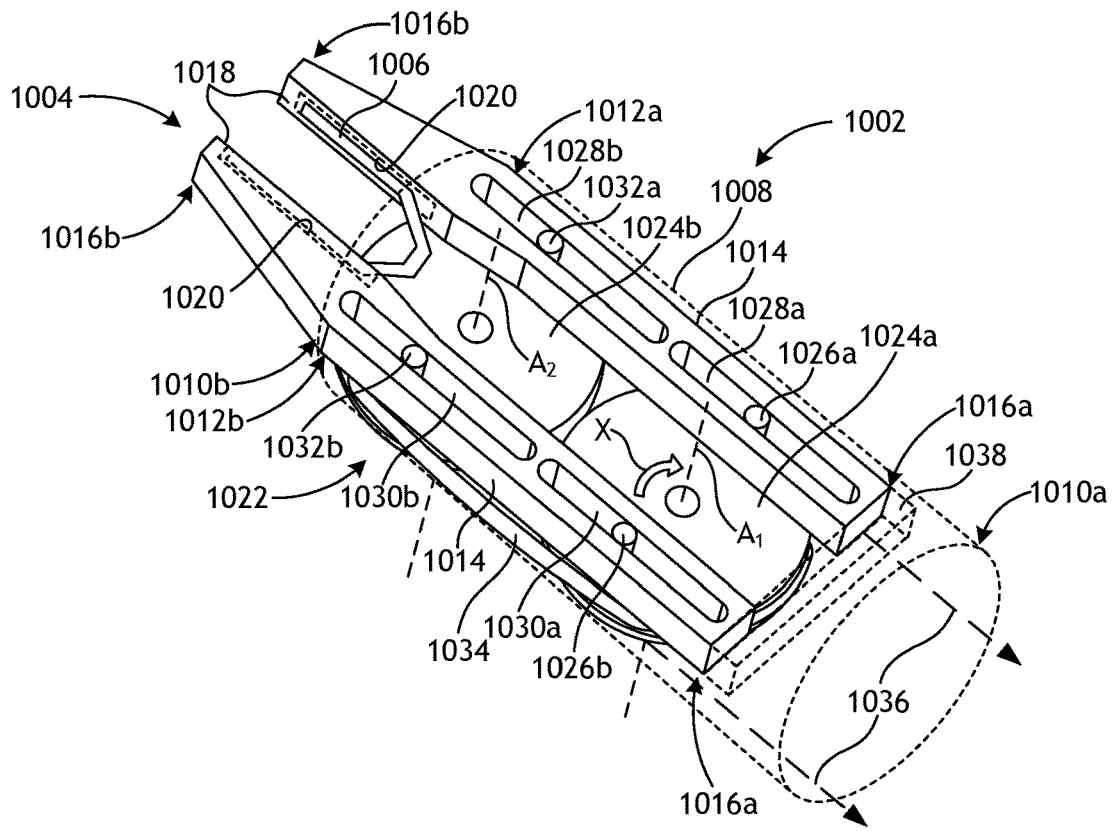
FIGS. 10A and 10B are isometric views of an example end effector that may incorporate the principles of the present disclosure.
Figure 10B:
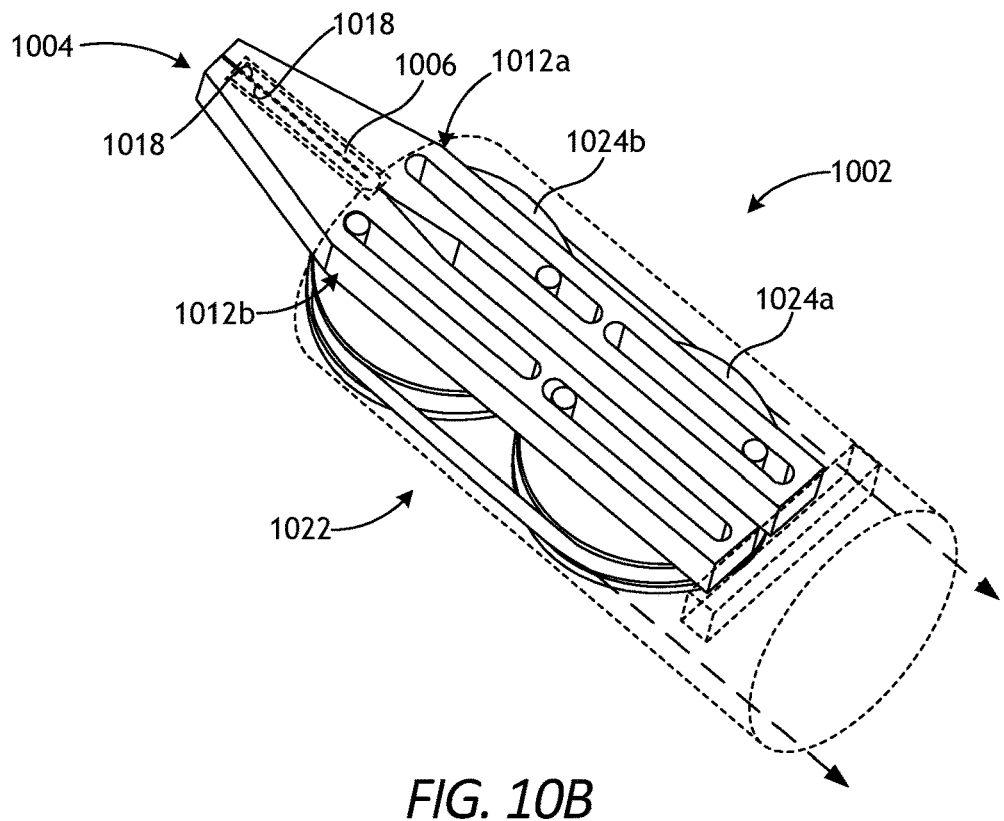

FIGS. 10A and 10B are isometric views of an example end effector 1002 that may incorporate the principles of the present disclosure, according to one or more embodiments. The end effector 1002 may be similar in some respects to the end effector 204 of FIG. 2 and, therefore, may be incorporated into the surgical tool 200 described herein above. Moreover, the end effector 1002 may comprise a clip applier having jaws 1004 that are actuatable to collapse toward one another to crimp a surgical clip 1006. The jaws 1004 may be similar in some respects to the jaws 412 of FIG. 6 and may, in at least one embodiment, replace the jaws 412 in any of the above-described embodiments.

FIGS. 10A and 10B illustrate progressive views of the end effector 1002 during example operation. More specifically, FIG. 10A shows the jaws 1004 in the open position, and FIG. 10B shows the jaws in the closed position. Referring first to FIG. 10A, the end effector 1002 may include a housing 1008 (shown in dashed) having a proximal end 1010a and a distal end 1010b. The housing 1008 may at least partially surround most of the component parts of the end effector. In some embodiments, the housing 1008 may form part of and otherwise comprise an axial extension of the outer tube 402 of FIG. 4. In other embodiments, however, the housing 1008 may comprise an independent structure from the outer tube 402. For example, in at least one embodiment the proximal end 1010a may be operatively coupled to an elongate shaft of a surgical tool, such as the shaft 202 of the surgical tool 200 of FIG. 2. In other embodiments, however, the proximal end 1010a may be operatively coupled to an articulable wrist joint that enables the end effector 1002 and related jaws 1004 to articulate during operation.

As illustrated, the jaws 1004 comprise a two-piece assembly that includes opposing jaw members 1012a and 1012b. The jaw members 1012a,b extend out of or otherwise protrude from the distal end 1010b of the housing 1008. Each jaw member 1012a,b is an independent structure that is movable relative to the other upon actuation to transition the jaws 1004 between the open and closed positions. As illustrated, each jaw member 1012a,b comprises an elongate body 1014 having a first or proximal end 1016a and a second or distal end 1016b. Surgical clips 1006 (one shown) may be received between the jaw members 1012a,b at or near the distal end 1016b for crimping. More specifically, surgical clips 1006 may be fed into and otherwise received between opposed inner surfaces 1018 of the jaw members 1012a,b provided at the distal end 1016b. In some embodiments, a groove 1020 may be defined on the inner surface 1018 of each jaw member 1012a,b at the distal end 1016b. Each groove 1020 may be configured to receive the opposing legs of the surgical clip 1006 in alignment with the jaw members 1012a,b. In other embodiments, however, the grooves 1020 may be omitted and the surgical clip 1006 may be maintained between the opposing inner surfaces 1018 via an interference fit or the like.

In contrast to the design and function of conventional jaws (e.g., the jaws 412 of FIGS. 4, 6, and 9A), which commonly employ one-piece opposing jaw members with a gap defined therebetween, the discrete and individual jaw members 1012a,b described herein allow the jaws 1004 to achieve parallel closure between the opposing inner surfaces 1018. Parallel closure of the opposing inner surfaces 1018 may prove advantageous in reducing the amount of force required to collapse the jaw members 1012a,b to the closed position.

As used herein, the phrase "parallel closure" refers to the relative parallel disposition of the opposing inner surfaces 1018 of the jaw members 1012a,b throughout the entire range of motion as the jaw members 1012a,b move between open and closed positions. "Parallel closure" is often used with respect to medical device end effectors and is desirable to minimize tissue damage due to non-uniform pressure or milking (squeezing out) of tissue from between opposed jaw members. Because the jaw members 1012a,b are separate and independent structures that are movable relative to one another during actuation, the inner surfaces 1018 are able to maintain a parallel or substantially parallel correlation (juxtaposition) while collapsing toward the closed position and crimping the surgical clip 1006.

The end effector 1002 may further include an actuation mechanism 1022 operatively coupled to the jaw members 1012a,b and actuatable to transition the jaw members 1012a,b between the open and closed positions. As used herein, the phrase "operatively coupled" can refer to a direct or indirect coupling relationship between two structural members. In the illustrated embodiment, the actuation mechanism 1022 includes a dual-pulley assembly comprising a first or proximal pulley 1024a and a second or distal pulley 1024b. The proximal and distal pulleys 1024a,b may be rotatably mounted within the housing 1008 and are each rotatable about corresponding central axes $A_1$ and $A_2$, respectively. In some embodiments, the proximal and distal pulleys 1024a,b may reside in the same plane within the end effector 1002 (i.e., coplanar), but may alternatively be arranged on different planes.

The proximal pulley 1024a provides or otherwise defines a first transition pin 1026a and a second transition pin 1026b located on angularly opposite sides of the proximal pulley 1024a. The first transition pin 1026a extends from the proximal pulley 1024a to slidably engage the first jaw member 1012a, and the second transition pin 1026b extends from the proximal pulley 1024a to slidably engage the second jaw member 1012b. More particularly, as illustrated, the first transition pin 1026a may be received within a first or proximal slot 1028a defined in the body 1014 of the first jaw member 1012a, and the second transition pin 1026b may be received within a first or proximal slot 1030a defined in the body 1014 of the second jaw member 1012b. As illustrated, the proximal slots 1028a, 1030a extend longitudinally and otherwise parallel to a longitudinal axis of the end effector 1002. As the jaws 1004 are actuated, the first and second transition pins 1026a,b slidably translate within the corresponding slots 1022a, 1030a, respectively.

Similarly, the distal pulley 1024b provides or otherwise defines a first transition pin 1032a and a second transition pin 1032b located on angularly opposite sides of the distal pulley 1024b. The first transition pin 1032a extends from the distal pulley 1024b to slidably engage the first jaw member 1012a, and the second transition pin 1032b extends from the distal pulley 1024b to slidably engage the second jaw member 1012b. More particularly, as illustrated, the first transition pin 1032a is received within a second or distal slot 1028b defined in the body 1014 of the first jaw member 1012a, and the second transition pin 1032b is received within a second or distal slot 1030b defined in the body 1014 of the second jaw member 1012b. As illustrated, the distal slots 1028b, 1030b extend longitudinally and otherwise parallel to the longitudinal axis of the end effector 1002. As the jaws 1004 are actuated, the first and second transition pins 1032a,b slidably translate within the corresponding slots 1028b, 1030b, respectively.

While each jaw member 1012a,b defines proximal and distal slots 1028a,b and 1030a,b, respectively, it is contemplated herein to include only a single slot on each jaw member 1012a,b. In such embodiments, the proximal and distal slots 1028a,b and 1030a,b of each jaw member 1012a,b, respectively, may be combined or otherwise merged to form a single slot into which the first and second transition pins 1026a,b and 1032a,b may extend and slidably engage the corresponding jaw members 1012a,b. Accordingly, the depiction of the separate proximal and distal slots 1028a,b and 1030a,b in each jaw member 1012a,b is merely for illustrative purposes and should not be considered limiting to the present disclosure.

Actuating the actuation mechanism 1022 causes the proximal and distal pulleys 1024a,b to simultaneously rotate about their respective central axes $A_1$, $A_2$, and thereby transition the jaws 1004 between the open and closed positions. In the illustrated embodiment, the proximal and distal pulleys 1024a,b are operatively coupled with a closed-loop actuation belt or cable 1034 wrapped or otherwise extending about each pulley 1024a,b in corresponding pulley grooves defined about the outer periphery of each pulley 1024a,b. Consequently, rotation of one of the proximal and distal pulleys 1024a,b in a first angular direction X will cause the actuation cable 1034 to move and correspondingly rotate the other of the proximal and distal pulleys 1024a,b in the same direction X, and vice versa. While the first angular direction X is shown in FIG. 10A as the clockwise direction, the first angular direction X may alternatively be the counter-clockwise direction, without departing from the scope of the disclosure.

The actuation mechanism 1022 may be configured to rotate the proximal pulley 1024a to simultaneously rotate the distal pulley 1024b and thereby cause actuation of the jaws 1004. In one embodiment, for example, one or more drive cables 1036 (shown in dashed) may loop around the proximal pulley 1024a in a separate pulley groove defined about the outer periphery (or at another location) of the proximal pulley 1024a. The drive cable(s) 1036 may extend to a drive housing (e.g., the drive housing 206 of FIG. 2) and be operatively coupled to a drive input that causes longitudinal movement of the drive cable(s) 1036. In at least one embodiment, for example, the drive cable(s) 1036 may be operatively coupled to one or more drive cable capstans arranged within the drive housing and rotation of the drive cable capstan(s) causes longitudinal movement of the drive cable(s) 1036 and, consequently, rotation of the proximal pulley 1024a. Moreover, in such embodiments, the drive cable(s) 1036 may be able to extend through an articulable wrist, if included in a given surgical tool.

In other embodiments, however, the actuation mechanism 1022 may include a gearing arrangement or mechanism configured to engage and rotate the proximal pulley 1024a. In such embodiments, for example, a drive shaft (not shown) may extend distally from a drive housing (e.g., the drive housing 206 of FIG. 2) and may be operatively coupled to an actuating mechanism or device at the drive housing and configured to cause rotation of the drive shaft. In one embodiment, for example, the drive shaft may be operatively coupled to and otherwise extend from a helical gear arrangement, similar to the first drive and driven gears 502a, 504a of FIG. 5. A worm gear may be positioned at the distal end of the drive shaft and may be engageable with the proximal pulley 1024a. Accordingly, rotation of the drive shaft would correspondingly rotate the worm gear and thereby drive rotation of the proximal pulley 1024a. In embodiments with an articulable wrist, the drive shaft may be made of a flexible material and capable of extending through the wrist.

While the actuation mechanism 1022 is described herein as being configured to rotate the proximal pulley 1024a to simultaneously rotate the distal pulley 1024b and thereby cause actuation of the jaws 1004, it is contemplated herein that the actuation mechanism 1022 may alternatively be configured to rotate the distal pulley 1024b to thereby rotate the proximal pulley 1024a and cause actuation of the jaws 1004, without departing from the scope of the disclosure. In such embodiments, the drive cable(s) 1036 or the gearing arrangement described above may instead be operatively coupled to the distal pulley 1024b to effect actuation of the jaws 1004.

Moreover, while the actuation mechanism 1022 is described and illustrated herein as including both the proximal and distal pulleys 1024a,b, it is contemplated herein to include only one pulley (e.g., the proximal pulley 1024a), without departing from the scope of the disclosure. In such embodiments, the drive cable(s) 1036 may be configured to rotate the proximal pulley 1024a, which causes the first and second transition pins 1026a,b to slidably translate within the corresponding slots 1022a, 1030a, respectively, and thereby collapse the jaw members 1012a,b toward each other.

Referring now to both FIGS. 10A and 10B, example operation of the end effector 1002 is now provided. FIG. 10A shows the jaws 1004 in the open position, and FIG. 10B depicts the jaws 1004 after having been moved (actuated) to a closed position.

In FIG. 10A, once the surgical clip 1006 is properly received between the jaw members 1012a,b at or near the distal end 1016b, the actuation mechanism 1022 may be actuated to rotate the proximal pulley 1024a about its central axis $A_1$ in the first angular direction X. Rotating the proximal pulley 1024a will drive the actuation cable 1034 linearly and thereby simultaneously rotate the distal pulley 1024b about its central axis $A_2$ in the first angular direction X. As the proximal and distal pulleys 1024a,b rotate, the first and second transition pins 1026a,b and 1032a,b of each pulley 1024a,b, respectively, will correspondingly rotate and slidably translate within the corresponding proximal and distal slots 1028a,b and 1030a,b defined in each jaw member 1012a,b. Continued angular rotation of the proximal and distal pulleys 1024a,b will progressively draw the jaw members 1012a,b toward each other as the first and second transition pins 1026a,b and 1032a,b slidably translate within the proximal and distal slots 1028a,b and 1030a,b.

In some embodiments, the jaws 1004 may be stabilized against longitudinal movement as the jaw members 1012a,b move toward or away from each other during actuation. In one embodiment, for example, the end effector 1002 may provide, define, or otherwise include a stop member 1038 (shown in dashed lines). The stop member 1038 may be fixed to or form an integral part of any stationary member or part of the end effector 1002. For instance, the stop member 1038 may be fixed or otherwise removably coupled to an inner wall of the housing 1008, which remains stationary during actuation. In the illustrated embodiment, the stop member 1038 is shown arranged at or near the proximal end 1016a of the jaws 1004, but may alternatively be positioned at any other location along the length of the jaw members 1012a,b. Moreover, while preventing the jaw members 1012a,b from moving longitudinally during actuation of the jaws 1004, the stop member 1038 may allow the jaw members 1012a,b to move laterally relative to one another.

FIG. 10B shows the surgical clip 1006 crimped between the opposing jaw members 1012a,b as the jaw members 1012a,b collapse toward each other during actuation. In some embodiments, the actuation mechanism 1022 may be programmed or otherwise operated to rotate the proximal and distal pulleys 1024a,b a predetermined or known angular distance that results in full crimping of the surgical clip 1006. Once the surgical clip 1006 is crimped, the actuation mechanism 1022 may be reversed to move the jaw members 1012a,b back to the open position in preparation for receiving another surgical clip.

Relative movement of the opposing jaw members 1012a,b allows the planar inner surfaces 1018 of each jaw member 1012a,b to approach each other in a parallel or substantially parallel trajectory, and thereby provides a simultaneous and uniform crimping of the surgical clip 1006. Compared to conventional clip applier jaws, the presently described jaws 1004 may prove advantageous for a variety of reasons. Conventional jaws have jaw members that act as cantilever beams as they are forced together during actuation. This results in the distal ends or tips of the jaw members touching first during actuation. Once the tips touch, the jaw members are effectively converted into continuous metal beams supported at each end instead of having a free end. As a result, a great deal of additional force is required to deform the middle of the jaw members to achieve full collapse of the jaws. Testing has shown that upwards of 70-80 lbf of force is required to fully collapse the jaw members of conventional jaws to crimp a surgical clip. The required elevated force necessitates more powerful actuators and more robust materials and manufacturing methods so that the jaws may withstand such forces.

In contrast, the presently described jaw members 1012a,b comprise separate structures that allow the jaws 1004 to achieve parallel closure and uniform crimping of the surgical clip 1006. Parallel closure dramatically reduces the force required to collapse the jaw members 1012a,b. In some applications, for example, the required force to adequately collapse (crimp) the surgical clip 1006 would be an order of magnitude or less than conventional jaws. This advantageously allows smaller actuators to be used to collapse the jaws 1004. Moreover, this allows the jaws 1004 to be made of less-expensive materials and manufactured through less-expensive manufacturing processes. In some embodiments, for example, the jaws 1004 may be made of injection molded plastic. In other embodiments, the jaws 1004 may be made of a metal and molded through a metal injection molding process. In yet other embodiments, the jaws 1004 may be made of a plastic or a metal and manufactured via an additive manufacturing process (e.g., 3D printing). In even further embodiments, the jaws 1004 may be made of a metallic base with a plastic overmolding, without departing from the scope of the disclosure.

The novel features of the jaws 1004 may also prove advantageous in helping to minimize the length and overall size of the jaws 1004. More specifically, since less force is required to collapse the jaws 1004, less jaw length is required to help deflect a cantilever beam-type jaw member. Consequently, the length of the jaws 1004 can be reduced, which may prove advantageous in minimizing the length of a clip applier past an articulation joint or wrist, for example. Another advantage of the separate jaw members 1012a,b is that surgical clips need not be introduced into the jaw members 1012a,b out of plane, i.e., from a different elevation within the end effector 1002. Rather, the surgical clips can be advanced distally in the same plane as the jaw members 1012a,b and pass between the space that separates the jaw members 1012a,b.

Figure 11A:
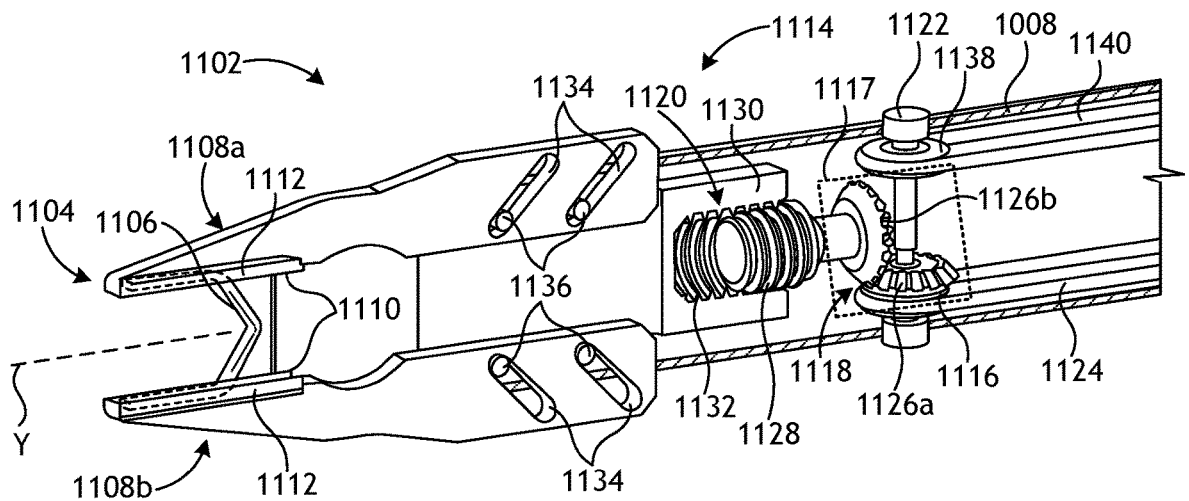
FIGS. 11A and 11B are partial cross-sectional views of another example end effector that may incorporate the principles of the present disclosure.
Figure 11B:
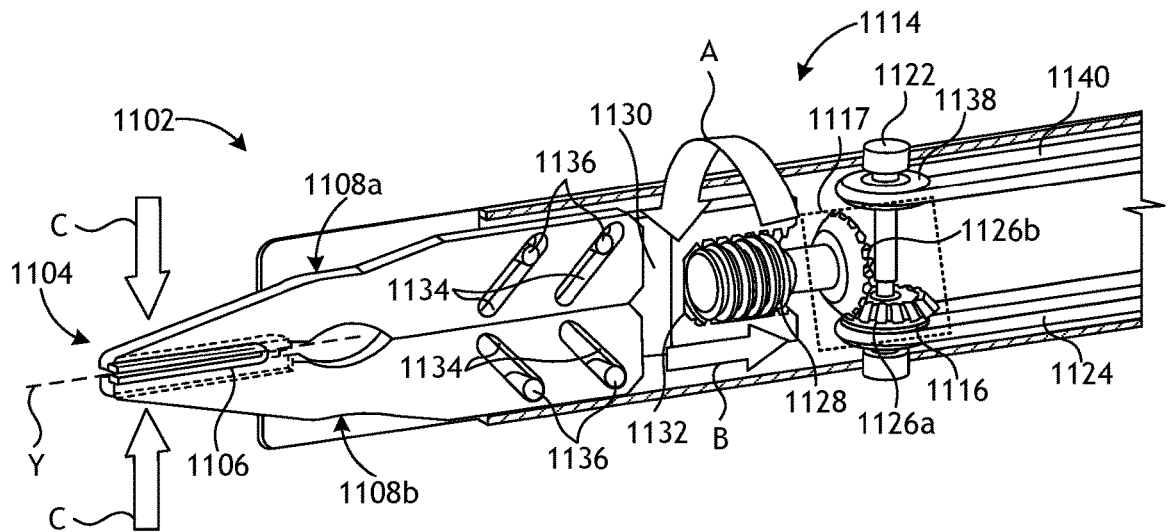

FIGS. 11A and 11B are partial cross-sectional views of another example end effector 1102 that may incorporate the principles of the present disclosure, according to one or more embodiments. The end effector 1102 may be similar in some respects to the end effector 1002 of FIGS. 10A-10B and therefore may also be incorporated into the surgical tool 200 described herein above. Moreover, the end effector 1102 may comprise a clip applier having jaws 1104 that are actuatable to collapse toward one another to crimp a surgical clip 1106.

The jaws 1104 may be similar in some respects to the jaws 1004 of FIGS. 10A-10B. For instance, similar to the jaws 1004, the jaws 1104 may also comprise a two-piece assembly that includes opposing jaw members 1108a and 1108b that are independent structures movable relative to the other upon actuation. Surgical clips 1106 may be fed into and otherwise received between opposed inner surfaces 1110 of the jaw members 1108a,b and, in some embodiments, a groove 1112 may be defined on the inner surface 1110 of each jaw member 1108a,b to receive the opposing legs of the surgical clip 1006. The discrete and individual jaw members 1108a,b described herein allow the jaws 1104 to achieve parallel closure between the opposing inner surfaces 1110.

The end effector 1102 may further include an actuation mechanism 1114 that may be actuatable to transition the jaw members 1108a,b between the open and closed positions. The actuation mechanism 1114 may comprise any device or mechanism capable of or configured to move (collapse) the jaw members 1108a,b toward each other and thereby crimp the surgical clip 1106 disposed therebetween. As illustrated, the actuation mechanism 1114 may include a jaw pulley 1116, a mechanical linkage 1117 operatively coupled to the jaw pulley 1116, and a linear drive 1120 operatively coupled to the mechanical linkage 1117. Rotation of the jaw pulley 1116 causes actuation of the mechanical linkage 1117, which, in turn, cause actuation of the linear drive 1120, which operates to collapse and open the jaw members 1108a,b.

More specifically, the jaw pulley 1116 may be rotatably mounted to an axle 1122 arranged within the housing 1008. A drive cable 1124 may be routed around the jaw pulley 1116 to cause rotation of the jaw pulley 1116. The drive cable 1124 may extend from a drive housing (e.g., the drive housing 206 of FIG. 2) and may be operatively coupled to a corresponding actuating mechanism or device positioned within the drive housing and configured to cause longitudinal translation of the drive cable 1124. In one embodiment, for example, the drive cable 1124 may be operatively coupled to one or more capstan pulleys. In other embodiments, the drive cable 1124 may be operatively coupled and otherwise extend from one or more translatable driven gears. In yet other embodiments, the drive cable 1124 may be operatively coupled to any combination of capstan pulley and driven gear, without departing from the scope of the disclosure.

The mechanical linkage 1117 can comprise any mechanical apparatus or configuration configured to convert the rotational movement of the jaw pulley 1116 into an axial load applied to the linear drive 1120. In some embodiments, for example, the mechanical linkage 1117 may comprise a U-joint, and rotation of the jaw pulley 1116 may actuate the U-joint to cause linear (axial) movement of the linear drive 1120 to move the first and second jaw members 1108a,b between the open and closed positions. In other embodiments, the mechanical linkage 1117 may comprise one or more cables threaded around a corner and wrapped directly onto a capstan arranged in axial alignment with linear drive. In such embodiments, rotation of the jaw pulley 1116 may drive the one or more cables to rotate the capstan, and thereby cause linear (axial) movement of the linear drive 1120 to move the first and second jaw members 1108a,b.

In yet other embodiments, as illustrated, the mechanical linkage 1117 may comprise a bevel gear assembly 1118. The bevel gear assembly 1118 may include a beveled drive gear 1126a coupled to or forming part of the jaw pulley 1116 and a corresponding beveled driven gear 1126b positioned to be driven (rotated) by the drive gear 1126a. In some embodiments, the linear drive 1120 may comprise a threaded linear drive that includes a worm gear 1128 operatively coupled to or extending from the driven gear 1126b, and a threaded gear plate 1130 that provides a female threading 1132 configured to threadably mate with or engage the helical threading defined on the worm gear 1128.

Referring now to both FIGS. 11A and 11B, example operation of the end effector 1102 is now provided. FIG. 11A shows the jaws 1104 in the open position, and FIG. 11B depicts the jaws 1004 after having been moved (actuated) to the closed position.

Once the surgical clip 1106 is properly received between the jaw members 1108a,b, the actuation mechanism 1114 may be actuated to commence collapsing the jaw members 1108a,b to crimp the surgical clip 1106. Triggering the actuation mechanism 1114 causes the drive cable 1124 to be translated (moved). As the drive cable 1124 translates, the jaw pulley 1116 and the drive gear 1126a are correspondingly rotated, and the drive gear 1126a transmits a rotational load to the driven gear 1126b, which correspondingly rotates in a first angular direction, as indicated by the arrow A (FIG. 11B). As the driven gear 1126b rotates, the helical threading on the worm gear 1128 interacts with the female threading 1132 on the gear plate 1130 and thereby urges (drives) the gear plate 1130 in a first linear direction, as indicated by the arrow B (FIG. 11B).

As illustrated, the jaw members 1108a,b comprise independent or separate plate-like structures that are configured to move laterally relative to one another to collapse and crimp the surgical clip 1106. As with the jaws 1004 of FIGS. 10A-10B, the jaws 1104 may be prevented from moving longitudinally during actuation. Each jaw member 1108a,b may provide and otherwise define one or more angled slots 1134 that extend at an angle offset from a longitudinal axis Y of the end effector 1102. While two angled slots 1134 are shown on each jaw member 1108a,b, it will be appreciated that more or less than two may be employed, without departing from the scope of the disclosure. The angled slots 1134 of each jaw member 1108a,b may extend at equal but opposite angles. More particularly, the slots 1134 of the first jaw member 1104 may extend at a positive angle relative to the longitudinal axis Y, while the slots 1134 of the second jaw member 1106 may extend at a negative angle of the same magnitude relative to the longitudinal axis Y. As a result, depending on the axial direction, the angled slots 1134 diverge from or converge toward each other along the longitudinal axis Y.

As illustrated, one or more transition pins 1136 extend from the gear plate 1130 and through the angled slots 1134 of each jaw member 1108a,b when the jaw members 1108a,b are installed in the end effector 1102. As the worm gear 1128 rotates, the gear plate 1130 correspondingly moves in the first linear direction B (FIG. 11B), which simultaneously moves the transition pins 1136 in the same direction. The transition pins 1136 slidingly engage the angled slots 1134 and, because of the oppositely angled configuration of the angled slots 1134, the transition pins 1136 will urge the jaw members 1108a,b to transition (move) laterally with respect to each other, as indicated by the oppositely directed arrows C (FIG. 11B). As the jaw members 1108a,b collapse toward each other in the direction C, the surgical clip 1106 will be crimped or crushed therebetween.

The jaw members 1108a,b may be re-opened to receive another un-crimped surgical clip by reversing the foregoing procedure. More specifically, the drive cable 1124 may be translated (moved) in a second driving direction opposite the first driving direction, which will rotate the jaw pulley 1116 and the drive gear 1126a in the opposite direction relative to the axle 1122, and the driven gear 1126b will correspondingly rotate in a second angular direction opposite the first angular direction A (FIG. 11B). Rotating the driven gear 1126b in the second angular direction will unthread the worm gear 1128 from the gear plate 1130, which urges (drives) the gear plate 1130 in a second linear direction opposite the first linear direction B (FIG. 11B). As the gear plate 1130 moves in the second linear direction, the transition pins 1136 also move in the same direction within and slidingly engaging the angled slots 1134, which urges the jaw members 1108a,b to separate from each other in a direction opposite the direction C.

In some embodiments, the actuation mechanism 1114 may further include a second jaw pulley 1138 rotatably mounted to the axle 1122 and a second drive cable 1140 may be routed around the second jaw pulley 1138 to cause rotation thereof. The second drive cable 1140 may be similar to the first drive cable 1124 and, therefore, may extend from a drive housing (e.g., the drive housing 206 of FIG. 2) and may be operatively coupled to a corresponding actuating mechanism or device positioned within the drive housing and configured to cause longitudinal translation of the second drive cable 1140. In at least one embodiment, actuation of the second drive cable 1140 may act on the mechanical linkage 1117 (e.g., the bevel gear assembly 1118) and thereby cause actuation of the jaws 1104. In such embodiments, the first drive cable 1124 may be actuated to close the jaws 1104, and the second drive cable 1140 may be actuated in the opposite direction to re-open the jaws 1104. The longitudinal movement of the drive cables 124, 1140 may be precisely controlled to collapse and open the jaw members 1108a,b to known magnitudes.

The independent or separate plate-like structures of the jaw members 1108a,b may exhibit similar advantages as described above with reference to the jaw members 1012a,b of FIGS. 10A-10B, and therefore will not be provided again.

Figure 12A:
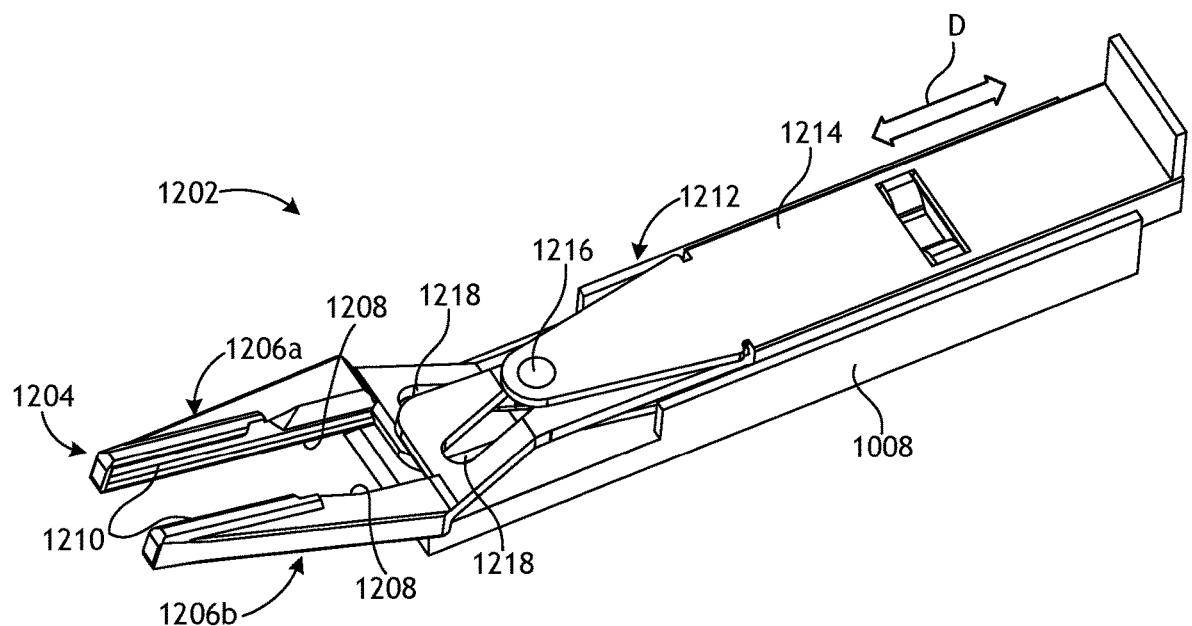
FIG. 12A is a partial isometric view of another example end effector that may incorporate the principles of the present disclosure

FIG. 12A is a partial isometric view of another example end effector 1202 that may incorporate the principles of the present disclosure, according to one or more embodiments. The end effector 1202 may be similar in some respects to the end effectors 1002 and 1102 of FIGS. 10A-10B and 11A-11B, respectively, and therefore may also be incorporated into the surgical tool 200 of FIG. 2 described herein. Moreover, the end effector 1202 may comprise a clip applier having jaws 1204 that are actuatable to collapse toward one another to crimp a surgical clip (not shown) therebetween.

Similar to the jaws 1004 and 1104 of FIGS. 10A-10B and 11A-11B, respectively, the jaws 1204 may also comprise a two-piece assembly that includes opposing jaw members 1206a and 1206b that are independent structures movable relative to the other upon actuation to achieve parallel closure. Surgical clips may be fed into and otherwise received between opposed inner surfaces 1208 of the jaw members 1206a,b, and in some embodiments, a groove 1210 may be defined on the inner surface 1110 of each jaw member 1206a,b and configured to receive the opposing legs of the surgical clip.

The end effector 1202 may further include an actuation mechanism 1212 that may be actuatable to transition the jaw members 1206a,b between the open and closed positions. The actuation mechanism 1212 may comprise any device or mechanism capable of or configured to move (collapse) the jaw members 1206a,b toward each other and thereby crimp the surgical clip disposed therebetween. In the illustrated embodiment, the actuation mechanism 1212 includes an actuation plate 1214 movably positioned (at least partially) within the housing 1008 and configured for longitudinal translation relative to the housing 1008 and the jaws 1204.

To facilitate longitudinal movement, the actuation plate 1214 may be operatively coupled to a drive mechanism (not shown) configured to move the actuation plate 1214 back and forth in the longitudinal directions D. In some embodiments, for example, a portion of the actuation plate 1214 may extend proximally to a drive housing (e.g., the drive housing 206 of FIG. 2) and may be operatively coupled to an actuating mechanism or device at the drive housing and configured to longitudinally translate the actuation plate 1214. In other embodiments, the actuation plate 1214 may be operatively coupled to a drive shaft that extends from the drive housing and is actuatable to facilitate longitudinal movement of the actuation plate 1214. In embodiments with an articulable wrist, the drive shaft may be made of a flexible material and capable of extending through the wrist.

As it translates longitudinally, the actuation plate 1214 may slidingly engage the jaw members 1206a,b and thereby cause the jaws 1204 to move between the open and closed positions, depending on the longitudinal translation direction D. More specifically, the actuation plate 1214 may include a transition pin 1216 that extends (e.g., downwardly) from the actuation plate 1214 and is received within corresponding slots 1218 defined in each jaw member 1206a,b. The slots 1218 each provide a profile configured to urge the jaw members 1206a,b to move laterally relative to the other as the transition pin 1216 traverses the slots 1218.

Figure 12B:
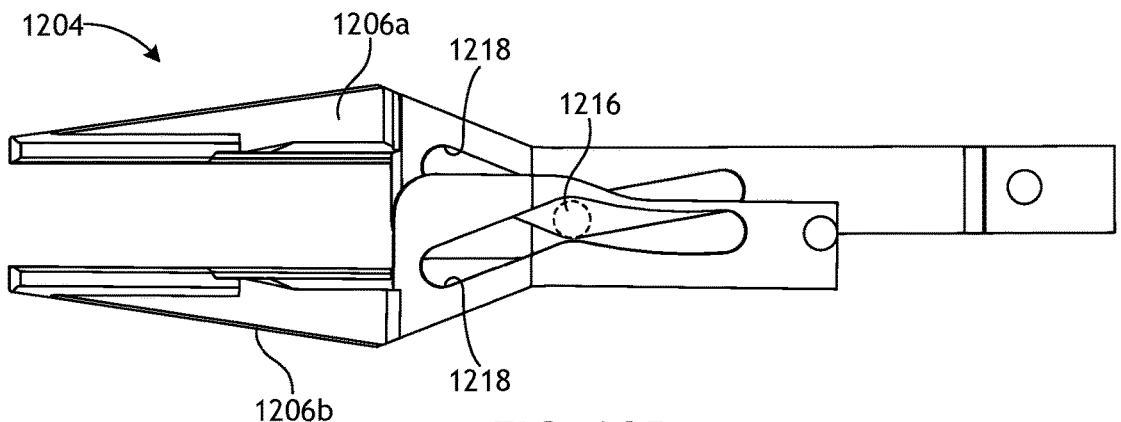
FIGS. 12B and 12C are top views of the jaws of FIG. 12A in the open and closed positions.
Figure 12C:
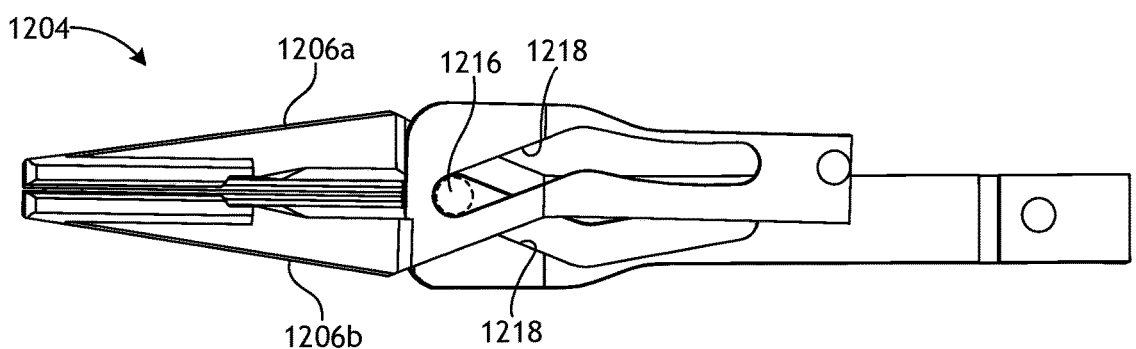

FIGS. 12B and 12C are top views of the jaws 1204 in the open and closed positions, respectively. As illustrated, the slots 1218 defined in each jaw member 1206a,b provide an angled profile and the transition pin 1216 (shown in dashed) extends into each slot 1218. As the transition pin 1216 moves distally within the slots 1218, the transition pin 1216 slidingly engages the angled profile and urges the jaw members 1206a,b to collapse toward each other. The jaws 1204 are moved back to the open position by moving the transition pin 1216 proximally within the slots 1218.

Figure 12D:
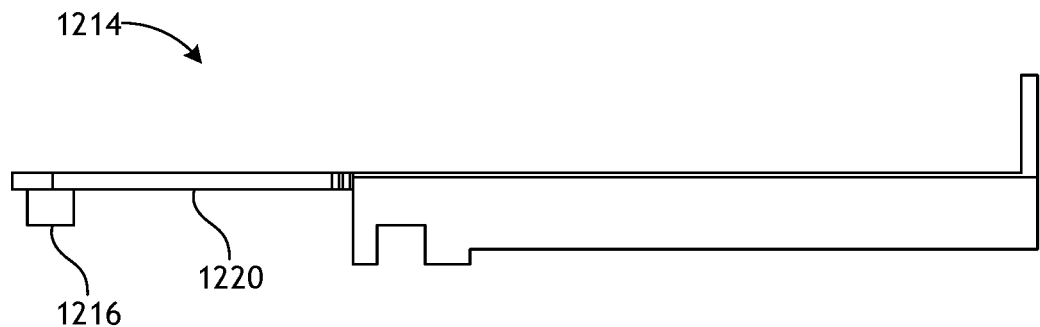
FIG. 12D is a side view of the actuation plate of FIG. 12A.

FIG. 12D is a side view of the actuation plate 1214, according to one or more embodiments. As illustrated, the transition pin 1216 extends downward from a bottom surface 1220 of the actuation plate 1214 to enable the transition pin 1216 to be received within the aligned slots 1218 (FIGS. 12A-12C) of the jaw members 1206a,b (FIGS. 12A-12C). The transition pin 1216 may be coupled to the actuation plate 1214 or otherwise form an integral extension thereof. In other embodiments, however, the actuation plate 1216 may be configured to be positioned beneath the jaw members 1206a,b in the end effector 1202 (FIG. 12A). In such embodiments, the transition pin 1216 may instead extend upward from a top surface of the actuation plate 1214.

It will be appreciated that the illustrated configuration of the actuation plate 1214 is only one example design thereof. Those skilled in the art will readily appreciate that several variations to the design may be employed without departing from the scope of the disclosure. Accordingly, the actuation plate 1214 is shown merely for illustrative purposes and should not be considered limiting to the present disclosure.

Figure 12E:
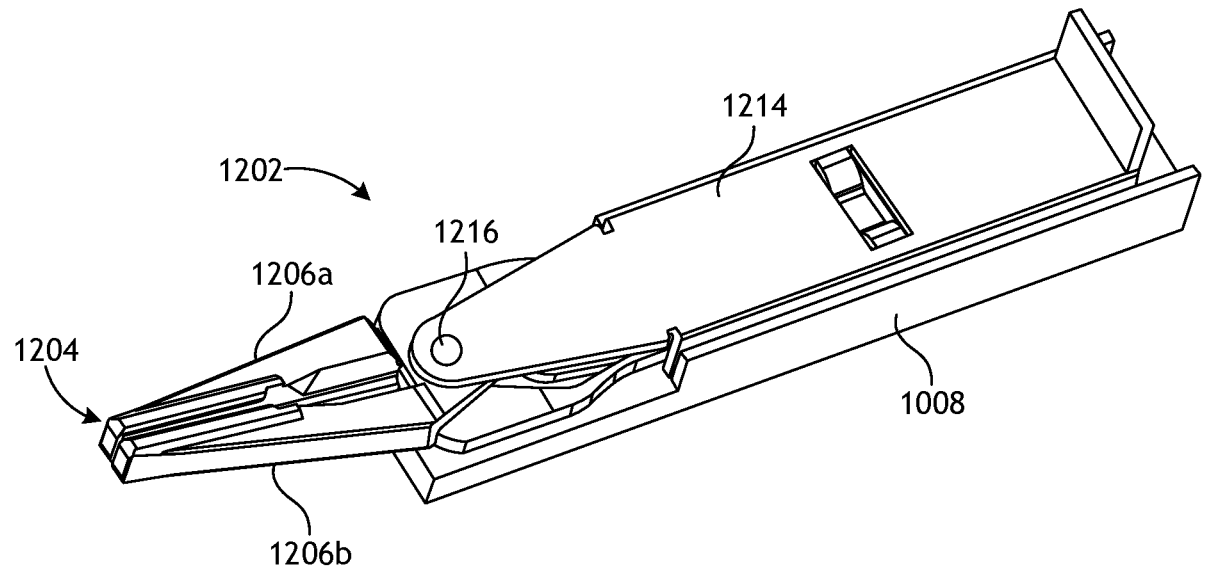
FIG. 12E is an isometric view of the end effector of FIG. 12A with the jaws in the closed position.

FIG. 12E is an isometric view of the end effector 1202 with the jaws 1204 moved to the closed position. As illustrated, the actuation plate 1214 has moved distally relative to the body 1008 and the jaws 1204. As the actuation plate 1214 moves distally, the transition pin 1216 slidingly translates within the corresponding slots 1218 defined in the jaw members 1206a,b, and the angled profile of the slots 1218 urges the jaw members 1206a,b to collapse toward each other.

Embodiments disclosed herein include:

A. An end effector for a surgical clip applier that includes a housing, jaws that extend past a distal end of the housing and include opposed first and second jaw members each comprising an independent structure movable relative to the other, the first jaw member defining a first inner surface and the second jaw member defining a second inner surface opposite the first inner surface, and an actuation mechanism operatively coupled to the jaw members to move the jaws between an open position and a closed position, wherein the first and second inner surfaces remain substantially parallel to each other as the jaws move between the open and closed positions.

B. A surgical clip applier that includes a drive housing, an elongate shaft that extends from the drive housing, and an end effector arranged at a distal end of the elongate shaft. The end effector includes a housing, jaws that extend past a distal end of the housing and include opposed first and second jaw members each comprising an independent structure movable relative to the other, the first jaw member defining a first inner surface and the second jaw member defining a second inner surface opposite the first inner surface, and an actuation mechanism operatively coupled to the jaw members to move the jaws between an open position and a closed position, wherein the first and second inner surfaces remain substantially parallel to each other as the jaws move between the open and closed positions.

C. A method of operating a surgical clip applier that includes positioning the surgical clip applier adjacent a patient for operation, the surgical clip applier including a drive housing, an elongate shaft that extends from the drive housing, and an end effector arranged at a distal end of the elongate shaft, the end effector including a housing, and jaws that extend past a distal end of the housing and include opposed first and second jaw members each comprising an independent structure movable relative to the other. The method further including actuating the surgical clip applier to move the first and second jaw members from an open position to a closed position, wherein the first jaw member provides a first inner surface and the second jaw member provides a second inner surface opposite the first inner surface, maintaining the first and second inner surfaces substantially parallel to each other as the first and second jaw members move to the closed position, and crimping a surgical clip disposed between the first and second jaw members.

Each of embodiments A, B, and C may have one or more of the following additional elements in any combination: Element 1: wherein the actuation mechanism comprises a first pulley rotatably mounted within the housing and providing a first transition pin slidably engageable with the first jaw member and a second transition pin slidably engageable with the second jaw member, and one or more drive cables operatively coupled to the first pulley and longitudinally movable to rotate the first pulley and thereby transition the jaws between the open and closed positions. Element 2: further comprising a second pulley rotatably mounted within the housing distal to the first pulley and providing a first transition pin slidably engageable with the first jaw member and a second transition pin slidably engageable with the second jaw member, and a closed-loop actuation cable wrapped about the first and second pulleys, wherein rotation of the first pulley correspondingly rotates the second pulley to transition the jaws between the open and closed positions. Element 3: wherein the first transition pin of the first pulley and the first transition pin of the second pulley are each received within one or more slots defined in the first jaw member, and wherein the second transition pin of the first pulley and the second transition pin of the second pulley are each received within one or more slots defined in the second jaw member. Element 4: wherein the actuation mechanism comprises a jaw pulley rotatably mounted to an axle arranged within the housing, a drive cable routed around the jaw pulley and longitudinally movable to rotate the jaw pulley, a mechanical linkage operatively coupled to the jaw pulley, and a linear drive having a gear plate operatively coupled to the mechanical linkage, wherein rotation of the jaw pulley actuates the mechanical linkage and thereby causes actuation of the linear drive, which operates to move the first and second jaw members between the open and closed positions. Element 5: further comprising one or more first angled slots defined in the first jaw member and extending at a positive angle relative to a longitudinal axis of the end effector, one or more second angled slots defined in the second jaw member and extending at a negative angle relative to the longitudinal axis, wherein the negative angle is of a same magnitude as the positive angle, and one or more transition pins extending from the gear plate and through the one or more first and second angled slots, wherein actuation of the linear drive moves the gear plate in a linear direction and correspondingly moves the one or more transition pins to slidingly engage the one or more first and second angled slots and thereby urges the first and second jaw members laterally with respect to each other. Element 6: wherein the actuation mechanism comprises an actuation plate movably positioned within the housing and adapted for longitudinal translation relative to the jaws, and a transition pin extending from the actuation plate and received within corresponding slots defined in each jaw member, wherein, as the transition pin traverses the corresponding slots in a longitudinal direction, the first and second jaw members are moved laterally relative to the other. Element 7: wherein the jaws are made of metal, plastic, or metal overmolded with plastic, and wherein the jaws are manufactured by one of machining, stamping, molding and an additive manufacturing process. Element 8: further comprising a groove defined in each of the first and second inner surfaces for receiving legs of a surgical clip.

Element 9: further comprising an articulable wrist joint interposing the end effector and the elongate shaft. Element 10: wherein the actuation mechanism comprises a first pulley rotatably mounted within the housing and providing a first transition pin slidably engageable with the first jaw member and a second transition pin slidably engageable with the second jaw member, and one or more drive cables operatively coupled to the first pulley and extending to the drive housing, wherein the one or more drive cables are longitudinally movable from the drive housing to rotate the first pulley and thereby transition the jaws between the open and closed positions. Element 11: further comprising a second pulley rotatably mounted within the housing distal to the first pulley and providing a first transition pin slidably engageable with the first jaw member and a second transition pin slidably engageable with the second jaw member, and a closed-loop actuation cable wrapped about the first and second pulleys, wherein rotation of one of the first pulley correspondingly rotates the second pulley to transition the jaws between the open and closed positions. Element 12: wherein the actuation mechanism comprises a jaw pulley rotatably mounted to an axle arranged within the housing, a drive cable routed around the jaw pulley and longitudinally movable to rotate the jaw pulley, a mechanical linkage operatively coupled to the jaw pulley, and a linear drive having a gear plate operatively coupled to the mechanical linkage, wherein rotation of the jaw pulley actuates the mechanical linkage and thereby causes actuation of the linear drive, which operates to move the first and second jaw members between the open and closed positions. Element 13: further comprising one or more first angled slots defined in the first jaw member and extending at a positive angle relative to a longitudinal axis of the end effector, one or more second angled slots defined in the second jaw member and extending at a negative angle relative to the longitudinal axis, wherein the negative angle is of a same magnitude as the positive angle, and one or more transition pins extending from the gear plate and through the one or more first and second angled slots, wherein actuation of the linear drive moves the gear plate in a linear direction and correspondingly moves the one or more transition pins to slidingly engage the one or more first and second angled slots and thereby urges the first and second jaw members laterally with respect to each other. Element 14: wherein the actuation mechanism comprises an actuation plate movably positioned within the housing and adapted for longitudinal translation relative to the jaws, wherein the actuation plate is actuatable from the drive housing, and a transition pin extending from the actuation plate and received within corresponding slots defined in each jaw member, wherein, as the transition pin traverses the corresponding slots in a longitudinal direction, the first and second jaw members are moved laterally relative to the other.

Element 15: wherein actuating the surgical clip applier is preceded by distally advancing the surgical clip in a same plane as the jaw members and thereby traversing a space that separates the first and second jaw members, and positioning the surgical clip between the first and second inner surfaces. Element 16: wherein actuating the surgical clip applier comprises triggering operation of an actuation mechanism that includes a pulley rotatably mounted within the housing and providing a first transition pin slidably engageable with the first jaw member and a second transition pin slidably engageable with the second jaw member, and one or more drive cables operatively coupled to the pulley and extending from the drive housing, and longitudinally moving the one or more drive cables and thereby rotating the first pulley and correspondingly moving the first and second jaw members from the open position to the closed position. Element 16: wherein actuating the surgical clip applier comprises triggering operation of an actuation mechanism that includes an actuation plate having a transition pin extending therefrom and received within corresponding slots defined in each jaw member, longitudinally moving the actuation plate relative to the first and second jaw members, and moving the first and second jaw members laterally relative to the other as the transition pin slidably translates within each slot.

By way of non-limiting example, exemplary combinations applicable to A, B, and C include: Element 1 with Element 2; Element 2 with Element 3; Element 4 with Element 5; Element 10 with Element 11; Element 12 with Element 13; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
a housing;
jaws that include opposed first and second jaw members each comprising an independent structure movable relative to the other, the first jaw member defining a first inner surface and the second jaw member defining a second inner surface opposite the first inner surface; and
an actuation mechanism operable to move the jaws between an open position and a closed position, the actuation mechanism including:
a linear drive that provides transition pins engageable with angled slots defined in the first and second jaw members;
a jaw pulley rotatably mounted within the housing; and
a mechanical linkage that operatively couples the jaw pulley to the linear drive,
wherein rotation of the jaw pulley actuates the mechanical linkage and thereby causes linear movement of the linear drive to move the first and second jaw members between the open and closed positions,
wherein the angled slots extend either away or toward a longitudinal axis of the end effector and linear movement of the linear drive moves the jaws between the open and closed positions, and
wherein the first and second inner surfaces remain substantially parallel to each other as the jaws move between the open and closed positions.

2. The end effector of claim 1, wherein the angled slots include one or more first angled slots defined in the first jaw member and one or more second angled slots defined in the second jaw member, and
wherein linear movement of the linear drive correspondingly moves the transition pins to slidingly engage the one or more first and second angled slots and thereby urges the first and second jaw members laterally with respect to each other.

3. The end effector of claim 2, wherein the one or more first angled slots extend at a positive angle relative to the longitudinal axis of the end effector, and the one or more second angled slots extend at a negative angle relative to the longitudinal axis, and wherein the negative angle is of a same magnitude as the positive angle.

4. The end effector of claim 1, wherein the mechanical linkage comprises a bevel gear assembly that includes a beveled drive gear coupled to the jaw pulley, and a beveled driven gear positioned to be driven by the drive gear, and
wherein the linear drive comprises a threaded linear drive that includes a worm gear extending from the driven gear, and a threaded gear plate that threadably mates with the worm gear.

5. The end effector of claim 1, wherein the jaw pulley is a first jaw pulley rotatably mounted to an axle within the housing, the end effector further comprising:
a first drive cable routed around the first jaw pulley and longitudinally movable to rotate the first jaw pulley;
a second jaw pulley rotatably mounted to the axle within the housing; and
a second drive cable routed around the second jaw pulley and longitudinally movable to rotate the second jaw pulley,
wherein actuation of the first drive cable closes the jaws and actuation of the second drive cable opens the jaws.

6. The end effector of claim 1, wherein the jaws are made of metal, plastic, or metal overmolded with plastic, and wherein the jaws are manufactured by one of machining, stamping, molding and an additive manufacturing process.

7. The end effector of claim 1, further comprising a groove defined in each of the first and second inner surfaces for receiving legs of a surgical clip.

8. A surgical clip applier, comprising:
a drive housing;
an elongate shaft that extends from the drive housing; and
an end effector arranged at a distal end of the elongate shaft, the end effector including:
a housing;
jaws that include opposed first and second jaw members each comprising an independent structure movable relative to the other, the first jaw member defining a first inner surface and the second jaw member defining a second inner surface opposite the first inner surface; and
an actuation mechanism operable to move the jaws between an open position and a closed position, the actuation mechanism including a linear drive that provides transition pins engageable with angled slots defined in the first and second jaw members, a jaw pulley rotatably mounted within the housing, and a mechanical linkage that operatively couples the jaw pulley to the linear drive, wherein rotation of the jaw pulley actuates the mechanical linkage and thereby causes linear movement of the linear drive to move the first and second jaw members between the open and closed positions, wherein the angled slots extend either away or toward a longitudinal axis of the end effector and linear movement of the linear drive moves the jaws between the open and closed positions, and wherein the first and second inner surfaces remain substantially parallel to each other as the jaws move between the open and closed positions.

9. The surgical clip applier of claim 8, wherein the angled slots include one or more first angled slots defined in the first jaw member and one or more second angled slots defined in the second jaw member, and wherein linear movement of the linear drive correspondingly moves the transition pins to slidingly engage the one or more first and second angled slots and thereby urges the first and second jaw members laterally with respect to each other.

10. The surgical clip applier of claim 9, wherein the one or more first angled slots extend at a positive angle relative to the longitudinal axis of the end effector, and the one or more second angled slots extend at a negative angle relative to the longitudinal axis, and wherein the negative angle is of a same magnitude as the positive angle.

11. The surgical clip applier of claim 8, wherein the mechanical linkage comprises a bevel gear assembly that includes a beveled drive gear coupled to the jaw pulley, and a beveled driven gear positioned to be driven by the drive gear, and wherein the linear drive comprises a threaded linear drive that includes a worm gear extending from the driven gear, and a threaded gear plate that threadably mates with the worm gear.

12. The surgical clip applier of claim 8, wherein the jaw pulley is a first jaw pulley rotatably mounted to an axle within the housing, the end effector further comprising:

a first drive cable routed around the first jaw pulley and longitudinally movable to rotate the first jaw pulley;

a second jaw pulley rotatably mounted to the axle within the housing; and a second drive cable routed around the second jaw pulley and longitudinally movable to rotate the second jaw pulley, wherein actuation of the first drive cable closes the jaws and actuation of the second drive cable opens the jaws.

13. The surgical clip applier of claim 8, wherein the jaws are made of metal, plastic, or metal overmolded with plastic, and wherein the jaws are manufactured by one of machining, stamping, molding and an additive manufacturing process.

14. A method of operating a surgical clip applier, comprising:

positioning the surgical clip applier adjacent a patient for operation, the surgical clip applier including a drive housing, an elongate shaft that extends from the drive housing, and an end effector arranged at a distal end of the elongate shaft, the end effector including:

a housing; and jaws that include opposed first and second jaw members each comprising an independent structure movable relative to the other, the first jaw member defining a first inner surface and the second jaw member defining a second inner surface opposite the first inner surface;

actuating an actuation mechanism arranged within the housing to move the first and second jaw members from an open position to a closed position, the actuation mechanism including:

a linear drive that provides transition pins engageable with angled slots defined in the first and second jaw members, wherein the angled slots extend either away or toward a longitudinal axis of the end effector, a jaw pulley rotatably mounted within the housing, and a mechanical linkage that operatively couples the jaw pulley to the linear drive;

maintaining the first and second inner surfaces substantially parallel to each other as the first and second jaw members move to the closed position; and crimping a surgical clip disposed between the first and second jaw members, wherein the actuation mechanism further includes, and wherein actuating the actuation mechanism comprises:

rotating the jaw pulley to actuate the mechanical linkage and thereby causing linear movement of the linear drive; and moving the first and second jaw members between the open and closed positions as the linear drive moves.

15. The method of claim 14, wherein actuating the surgical clip applier is preceded by:

distally advancing the surgical clip in a same plane as the jaw members and thereby traversing a space that separates the first and second jaw members; and positioning the surgical clip between the first and second inner surfaces.

16. The method of claim 14, wherein the angled slots include one or more first angled slots defined in the first jaw member and one or more second angled slots defined in the second jaw member, and wherein actuating the actuation mechanism comprises:

moving the linear drive linearly within the housing;

slidingly engaging the transition pins within the one or more first and second angled slots as the linear drive moves and thereby urging the first and second jaw members laterally with respect to each other.

17. The method of claim 14, wherein actuating the actuation mechanism further comprises:

rotating the jaw pulley to actuate the mechanical linkage and thereby causing linear movement of the linear drive; and moving the first and second jaw members between the open and closed positions as the linear drive moves.

* * * * *